(12) United States Patent
Hanger et al.

(10) Patent No.: US 8,748,700 B2
(45) Date of Patent: *Jun. 10, 2014

(54) CONTROL OF AAD-1 MONOCOT VOLUNTEERS IN FIELDS OF DICOT CROPS

(75) Inventors: Gregory A. Hanger, Carmel, IN (US); Andrew E. Robinson, Brownsburg, IN (US); Norbert M. Satchivi, Westfield, IN (US); Richard S. Chambers, Warriewood (AU); Terry R. Wright, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/390,988

(22) PCT Filed: Aug. 18, 2010

(86) PCT No.: PCT/US2010/045870
§ 371 (c)(1),
(2), (4) Date: May 7, 2012

(87) PCT Pub. No.: WO2011/022470
PCT Pub. Date: Feb. 24, 2011

(65) Prior Publication Data
US 2012/0220460 A1 Aug. 30, 2012

Related U.S. Application Data

(60) Provisional application No. 61/328,944, filed on Apr. 28, 2010, provisional application No. 61/235,248, filed on Aug. 19, 2009.

(51) Int. Cl.
*C12N 15/82* (2006.01)

(52) U.S. Cl.
USPC .......................................... 800/300; 800/288

(58) Field of Classification Search
USPC ........................................................ 800/300
See application file for complete search history.

(56) References Cited

U.S. PATENT DOCUMENTS

| 7,838,733 B2 * | 11/2010 | Wright et al. | 800/300 |
| 2007/0089201 A1 | 4/2007 | Briggs et al. | |
| 2009/0093366 A1 | 4/2009 | Wright et al. | |

FOREIGN PATENT DOCUMENTS

| WO | WO 99/45781 A1 | 9/1999 |
| WO | WO 2005/107437 A2 | 11/2005 |
| WO | WO 2007/053482 A2 | 5/2007 |
| WO | WO 2008/143993 A2 | 11/2008 |

OTHER PUBLICATIONS

Hohe et al, A tool for understanding homologous recombination in plants (2003) Plant Cell Rep. 21:1135-1142.*
Deen et al, Control of volunteer glyphosate-resistant corn (Zea mays) in glyphosate-resistant soybean (2006) Weed Tech. 20:261-266.*
Loux et al, Weed control guide for Ohio and Indiana (Jan. 23, 2009), published by Ohio State University.*
Chander, et al., Genetic dissection of tocopherol content and composition in maize grain using quantitative trait locai analysis and the candidate gene approach, Molecular Breeding, vol. 22, No. 3, Apr. 12, 2008, pp. 353-365.
Zhang, et al., Mapping quantitative trait loci for oil, starch, and protein concentrations in grain with high-oil maize by SSR markers, Euphytica, Kluwer Academic Publishers, vol., 162, No. 3, Aug. 3, 2007, pp. 335-344.
Antonius J.M. Matzke et al, Position effects and epigenetic silencing of plant transfenes, Current Opinion in Plant Biology, vol. 1, No. 2, Apr. 1, 1998, pp. 142-148.
Dow Chemical Japan Ltd., "Approved Type 1 Use Regulation: Maize tolerant to aryloxyalkanoate herbicide (Modified aad-1, Zea mays subsp.," Japan Biosafety Clearing House, Online Jul. 30, 2009, pdf also available at <url:http://www.bch.biodic.go.jp/english/lmo_2009.html>.
Tan et al., "Imidazolinone-tolerant crops: history, current status and future," Pest Manag Sci, Online Dec. 31, 2004, pp. 246-257, vol. 61, Issue 3.

* cited by examiner

*Primary Examiner* — David H Kruse
*Assistant Examiner* — Mykola Kovalenko
(74) *Attorney, Agent, or Firm* — James Daly; Kenneth B. Ludwig; Faegre Baker Daniels LLP

(57) ABSTRACT

The subject invention relates in part to the control of AAD-1 monocot volunteers in fields planted with dicot crops such as soybeans or cotton. According to some embodiments of the subject invention, cyclohexanedione herbicides are selected as being an effective tool for controlling AAD-1 volunteers, as AAD genes do not impart tolerance to this class of graminicide chemistry. In addition, imidazolinone-class herbicides can be used in some preferred embodiments for selective control of conventional or herbicide-tolerant varieties of volunteer corn. AAD-1 corn comprising Event DAS-40278-9 is used in some particularly preferred embodiments.

21 Claims, No Drawings

SEQUENCE LISTING

<160> NUMBER OF SEQ ID NOS: 4

<210> SEQ ID NO 1
<211> LENGTH: 295
<212> TYPE: PRT
<213> ORGANISM: Sphingobium herbicidovorans

<400> SEQUENCE: 1

```
Met His Ala Ala Leu Ser Pro Leu Ser Gln Arg Phe Glu Arg Ile Ala
1               5                   10                  15

Val Gln Pro Leu Thr Gly Val Leu Gly Ala Glu Ile Thr Gly Val Asp
                20                  25                  30

Leu Arg Glu Pro Leu Asp Asp Ser Thr Trp Asn Glu Ile Leu Asp Ala
            35                  40                  45

Phe His Thr Tyr Gln Val Ile Tyr Phe Pro Gly Gln Ala Ile Thr Asn
        50                  55                  60

Glu Gln His Ile Ala Phe Ser Arg Arg Phe Gly Pro Val Asp Pro Val
65                  70                  75                  80

Pro Leu Leu Lys Ser Ile Glu Gly Tyr Pro Glu Val Gln Met Ile Arg
                85                  90                  95

Arg Glu Ala Asn Glu Ser Gly Arg Val Ile Gly Asp Asp Trp His Thr
            100                 105                 110

Asp Ser Thr Phe Leu Asp Ala Pro Pro Ala Ala Val Val Met Arg Ala
        115                 120                 125

Ile Asp Val Pro Glu His Gly Gly Asp Thr Gly Phe Leu Ser Met Tyr
    130                 135                 140

Thr Ala Trp Glu Thr Leu Ser Pro Thr Met Gln Ala Thr Ile Glu Gly
145                 150                 155                 160

Leu Asn Val Val His Ser Ala Thr Arg Val Phe Gly Ser Leu Tyr Gln
                165                 170                 175

Ala Gln Asn Arg Arg Phe Ser Asn Thr Ser Val Lys Val Met Asp Val
            180                 185                 190

Asp Ala Gly Asp Arg Glu Thr Val His Pro Leu Val Val Thr His Pro
        195                 200                 205
```

```
Gly Ser Gly Arg Lys Gly Leu Tyr Val Asn Gln Val Tyr Cys Gln Arg
        210                 215                 220

Ile Glu Gly Met Thr Asp Ala Glu Ser Lys Pro Leu Leu Gln Phe Leu
225                 230                 235                 240

Tyr Glu His Ala Thr Arg Phe Asp Phe Thr Cys Arg Val Arg Trp Lys
                245                 250                 255

Lys Asp Gln Val Leu Val Trp Asp Asn Leu Cys Thr Met His Arg Ala
            260                 265                 270

Val Pro Asp Tyr Ala Gly Lys Phe Arg Tyr Leu Thr Arg Thr Thr Val
        275                 280                 285

Gly Gly Val Arg Pro Ala Arg
        290                 295

<210> SEQ ID NO 2
<211> LENGTH: 295
<212> TYPE: PRT
<213> ORGANISM: Artificial Sequence
<220> FEATURE:
<223> OTHER INFORMATION: AAD-1 v2 Translation
<220> FEATURE:
<221> NAME/KEY: MISC_FEATURE
<222> LOCATION: (2)..(2)
<223> OTHER INFORMATION: Different from v1
<220> FEATURE:
<221> NAME/KEY: MISC_FEATURE
<222> LOCATION: (212)..(212)
<223> OTHER INFORMATION: Different from v1

<400> SEQUENCE: 2

Met Ala Ala Ala Leu Ser Pro Leu Ser Gln Arg Phe Glu Arg Ile Ala
1               5                   10                  15

Val Gln Pro Leu Thr Gly Val Leu Gly Ala Glu Ile Thr Gly Val Asp
            20                  25                  30

Leu Arg Glu Pro Leu Asp Asp Ser Thr Trp Asn Glu Ile Leu Asp Ala
        35                  40                  45

Phe His Thr Tyr Gln Val Ile Tyr Phe Pro Gly Gln Ala Ile Thr Asn
    50                  55                  60

Glu Gln His Ile Ala Phe Ser Arg Arg Phe Gly Pro Val Asp Pro Val
65                  70                  75                  80

Pro Leu Leu Lys Ser Ile Glu Gly Tyr Pro Glu Val Gln Met Ile Arg
                85                  90                  95

Arg Glu Ala Asn Glu Ser Gly Arg Val Ile Gly Asp Asp Trp His Thr
            100                 105                 110

Asp Ser Thr Phe Leu Asp Ala Pro Ala Ala Val Val Met Arg Ala
        115                 120                 125

Ile Asp Val Pro Glu His Gly Gly Asp Thr Gly Phe Leu Ser Met Tyr
    130                 135                 140

Thr Ala Trp Glu Thr Leu Ser Pro Thr Met Gln Ala Thr Ile Glu Gly
145                 150                 155                 160

Leu Asn Val Val His Ser Ala Thr Arg Val Phe Gly Ser Leu Tyr Gln
                165                 170                 175

Ala Gln Asn Arg Arg Phe Ser Asn Thr Ser Val Lys Val Met Asp Val
            180                 185                 190

Asp Ala Gly Asp Arg Glu Thr Val His Pro Leu Val Val Thr His Pro
        195                 200                 205

Gly Ser Gly Cys Lys Gly Leu Tyr Val Asn Gln Val Tyr Cys Gln Arg
    210                 215                 220

Ile Glu Gly Met Thr Asp Ala Glu Ser Lys Pro Leu Leu Gln Phe Leu
225                 230                 235                 240
```

```
Tyr Glu His Ala Thr Arg Phe Asp Phe Thr Cys Arg Val Arg Trp Lys
                245                 250                 255

Lys Asp Gln Val Leu Val Trp Asp Asn Leu Cys Thr Met His Arg Ala
            260                 265                 270

Val Pro Asp Tyr Ala Gly Lys Phe Arg Tyr Leu Thr Arg Thr Thr Val
        275                 280                 285

Gly Gly Val Arg Pro Ala Arg
        290                 295

<210> SEQ ID NO 3
<211> LENGTH: 296
<212> TYPE: PRT
<213> ORGANISM: Artificial Sequence
<220> FEATURE:
<223> OTHER INFORMATION: AAD-1 v3 Translation
<220> FEATURE:
<221> NAME/KEY: MISC_FEATURE
<222> LOCATION: (2)..(3)
<223> OTHER INFORMATION: Different from V1

<400> SEQUENCE: 3

Met Ala His Ala Ala Leu Ser Pro Leu Ser Gln Arg Phe Glu Arg Ile
1               5                   10                  15

Ala Val Gln Pro Leu Thr Gly Val Leu Gly Ala Glu Ile Thr Gly Val
            20                  25                  30

Asp Leu Arg Glu Pro Leu Asp Asp Ser Thr Trp Asn Glu Ile Leu Asp
        35                  40                  45

Ala Phe His Thr Tyr Gln Val Ile Tyr Phe Pro Gly Gln Ala Ile Thr
    50                  55                  60

Asn Glu Gln His Ile Ala Phe Ser Arg Arg Phe Gly Pro Val Asp Pro
65                  70                  75                  80

Val Pro Leu Leu Lys Ser Ile Glu Gly Tyr Pro Glu Val Gln Met Ile
                85                  90                  95

Arg Arg Glu Ala Asn Glu Ser Gly Arg Val Ile Gly Asp Asp Trp His
            100                 105                 110

Thr Asp Ser Thr Phe Leu Asp Ala Pro Pro Ala Ala Val Val Met Arg
        115                 120                 125

Ala Ile Asp Val Pro Glu His Gly Gly Asp Thr Gly Phe Leu Ser Met
    130                 135                 140

Tyr Thr Ala Trp Glu Thr Leu Ser Pro Thr Met Gln Ala Thr Ile Glu
145                 150                 155                 160

Gly Leu Asn Val Val His Ser Ala Thr Arg Val Phe Gly Ser Leu Tyr
                165                 170                 175

Gln Ala Gln Asn Arg Arg Phe Ser Asn Thr Ser Val Lys Val Met Asp
            180                 185                 190

Val Asp Ala Gly Asp Arg Glu Thr Val His Pro Leu Val Val Thr His
        195                 200                 205

Pro Gly Ser Gly Arg Lys Gly Leu Tyr Val Asn Gln Val Tyr Cys Gln
    210                 215                 220

Arg Ile Glu Gly Met Thr Asp Ala Glu Ser Lys Pro Leu Leu Gln Phe
225                 230                 235                 240

Leu Tyr Glu His Ala Thr Arg Phe Asp Phe Thr Cys Arg Val Arg Trp
                245                 250                 255

Lys Lys Asp Gln Val Leu Val Trp Asp Asn Leu Cys Thr Met His Arg
            260                 265                 270
```

```
Ala Val Pro Asp Tyr Ala Gly Lys Phe Arg Tyr Leu Thr Arg Thr Thr
    275                 280                 285

Val Gly Gly Val Arg Pro Ala Arg
    290                 295

<210> SEQ ID NO 4
<211> LENGTH: 8557
<212> TYPE: DNA
<213> ORGANISM: Artificial Sequence
<220> FEATURE:
<223> OTHER INFORMATION: AAD-1 insert and flanking sequences

<400> SEQUENCE: 4
actggtattt aatatacttt aataaatatt attagattcc tcgtcaaaga acttttttaca       60 atatatctat ttagaatcat atatgtcata gttttttttc taagagtcta gtttactagt      120
aaaatccgac tcacattttt cgaacttggg atgcaacact taaatagtac aaaaccttgg      180
tatgcagtat tttacattgt aagattcaaa atttctaaag cagtatatat atgtttccag      240
aaacttatag atatagaaaa aacagagaga cgtatgcgaa aattcgataa aggtgtacat      300
tggattcgca aggctaaata catatttatc gtggatccat gcagagtttg ggtaataaaa      360
ttagatactt ccaatcatgt gccacataat cacgtaacat tagtaattta aatgacatta      420
ccatgtccaa ctgatttaaa acacaaactc ttcttgaacc atatagtttg acaaaccaaa      480
tatatataac tggagctact agttatgaat caattaaaaa ttactttgaa gattcaacgt      540
agtgccagtt tggctctagc acatctaacc agaagggcta aggctggctt caacaggaac      600
agccaaatcc gagatcgagc catttgccat ttttgggtag ttagtttaac tttcatatat      660
cttcccatcc ttttttgcct agcctaaatg gctttgatgt tgaagaccat attaatttgc      720
ttcagtggca ctaggacaac catattggct ttggctgacc cgttagagtt agcctaatgg      780
gtggaagggg agggaagggg aggatcgatg gtggcatgag agaggggttg acgatcacga      840
tgatgatgcg agtgaggagg agagggtggc gacgacacag gggagaaagg agagggacgc      900
taggagcgtc aagggcgtgg gggaggggag ggtcggaggg atgaaggatg acctaaaatat      960 tattgttgag tgatagaggg ttattcaact atccgacccg tcgattttga tggtatgtta     1020
aatttgtgtg tcatttgttt gatggattta gtaaaggtta tgggtctaga ggtgattttt     1080
gttgggtggg ttttacagag tttaaactag cggattatat agtggtatag aagatatagt     1140
tttattagaa catctccaaa atgtgactcg aaataatacc cccaaaattt aaaatactac     1200
atcattttga taaaaaaggt aaagtagagc actgttggaa cagttttttaa aagttgtgcc     1260 ctatatttta aaatagggta ctgatttaaa atattgttgt gggggataga tatccccggg     1320
tccactagaa ggcgagaagg cctcgcgtgt ggccacgggc cagttacccc gcaaggccat     1380
cccttcgtgg gtcgagctag aattactggt agaatgggct gaccgaagaa ggcaacagac     1440
tcgagcccaa acaatccatc ggctcgtgcg ctatccacag aaactacccg actttccggc     1500
gcatggcatc ctagaatatc ggggcgtatt agggatgagt cagcgagatt ttcggaagat     1560
tagttcagtt tgttcgctat tatttaggag acatatgatc ctcatgtacg tatggagtgc     1620
cccacggtcg tgtatataag gtccagaggg taccccatca tttctatcga ccatctacct     1680
atctcatcag ctttttctcca ttcaggagac ctcgcttgta acccaccaca tatagatcca     1740
tcccaagaag tagtgtatta cgcctctcta agcggcccaa acttgcagaa aaccgcctat     1800
ccctctctcg tgcgtccagc acgaaccatt gagttacaat caacagcacc gtaccttgaa     1860
gcggaataca atgaaggtta gctacgattt acagcaaagc cagaatacaa tgaaccataa     1920
```

```
agtgattgaa gctcgaaata tacgaaggaa caaatatttt taaaaaaata cgcaatgact   1980
tggaacaaaa gaaagtgata tattttttgt tcttaaacaa gcatcccctc taaagaatgg   2040
cagtttcct ttgcatgtaa ctattatgct cccttcgtta caaaaatttt ggactactat    2100
tgggaacttc ttctgaaaat agtggccacc gcttaattaa ggcgcgccat gcccgggcaa   2160
gcggccgctt aattaaattt aaatgtttaa actaggaaat ccaagcttgc atgcctgcag   2220
atccccgggg atcctctaga gtcgacctgc agtgcagcgt gacccggtcg tgcccctctc   2280
tagagataat gagcattgca tgtctaagtt ataaaaaatt accacatatt ttttttgtca   2340
cacttgtttg aagtgcagtt tatctatctt tatacatata tttaaacttt actctacgaa   2400
taatataatc tatagtacta caataatatc agtgttttag agaatcatat aaatgaacag   2460
ttagacatgg tctaaaggac aattgagtat tttgacaaca ggactctaca gttttatctt   2520
tttagtgtgc atgtgttctc cttttttttt gcaaatagct tcacctatat aatacttcat   2580
ccatttatt agtacatcca tttagggttt agggttaatg ttttatag actaattttt      2640
ttagtacatc tattttattc tattttagcc tctaaattaa gaaaactaaa actctatttt   2700
agtttttta tttaatagtt tagatataaa atagaataaa ataaagtgac taaaaattaa    2760
acaaataccc tttaagaaat taaaaaaact aaggaaacat ttttcttgtt tcgagtagat   2820
aatgccagcc tgttaaacgc cgtcgacgag tctaacggac accaaccagc gaaccagcag   2880
cgtcgcgtcg ggccaagcga agcagacggc acggcatctc tgtcgctgcc tctggacccc   2940
tctcgagagt tccgctccac cgttggactt gctccgctgt cggcatccag aaattgcgtg   3000
gcggagcggc agacgtgagc cggcacggca ggcggcctcc tcctcctctc acggcaccgg   3060
cagctacggg ggattccttt cccaccgctc cttcgctttc ccttcctcgc cgccgtaat   3120
aaatagacac cccctccaca ccctctttcc ccaacctcgt gttgttcgga gcgcacacac   3180
acacaaccag atctccccca aatccacccg tcggcacctc cgcttcaagg tacgccgctc   3240
gtcctccccc ccccccccc tctctacctt ctctagatcg gcgttccggt ccatgcatgg    3300
ttagggcccg gtagttctac ttctgttcat gtttgtgtta gatccgtgtt tgtgttagat   3360
ccgtgctgct agcgttcgta cacgatgcg acctgtacgt cagacacgtt ctgattgcta    3420
acttgccagt gtttctcttt ggggaatcct gggatggctc tagccgttcc gcagacggga   3480
tcgatttcat gattttttt gtttcgttgc atagggtttg gtttgccctt ttcctttatt    3540
tcaatatatg ccgtgcactt gtttgtcggg tcatcttttc atgcttttt ttgtcttggt    3600
tgtgatgatg tggtctggtt gggcggtcgt tctagatcgg agtagaattc tgtttcaaac   3660
tacctggtgg atttattaat tttggatctg tatgtgtgtg ccatacatat tcatagttac   3720
gaattgaaga tgatggatgg aaatatcgat ctaggatagg tatacatgtt gatgcgggtt   3780
ttactgatgc atatacagag atgctttttg ttcgcttggt tgtgatgatg tggtgtggtt   3840
gggcggtcgt tcattcgttc tagatcggag tagaatactg tttcaaacta cctggtgtat   3900
ttattaattt tggaactgta tgtgtgtgtc atacatcttc atagttacga gtttaagatg   3960
gatggaaata tcgatctagg ataggtatac atgttgatgt gggttttact gatgcatata   4020
catgatggca tatgcagcat ctattcatat gctctaacct tgagtaccta tctattataa   4080
taaacaagta tgttttataa ttatttcgat cttgatatac ttggatgatg gcatatgcag   4140
cagctatatg tggattttt tagccctgcc ttcatacgct atttatttgc ttggtactgt    4200
ttcttttgtc gatgctcacc ctgttgtttg gtgttacttc tgcagggtac ccccggggtc   4260
gaccatggct catgctgccc tcagccctct ctcccaacgc tttgagagaa tagctgtcca   4320
```

```
gccactcact ggtgtccttg gtgctgagat cactggagtg gacttgaggg aaccacttga    4380
tgacagcacc tggaatgaga tattggatgc cttccacact taccaagtca tctactttcc    4440
tggccaagca atcaccaatg agcagcacat tgcattctca agaaggtttg gaccagttga    4500
tccagtgcct cttctcaaga gcattgaagg ctatccagag gttcagatga tccgcagaga    4560
agccaatgag tctggaaggg tgattggtga tgactggcac acagactcca ctttccttga    4620
tgcacctcca gctgctgttg tgatgagggc catagatgtt cctgagcatg gcggagacac    4680
tgggttcctt tcaatgtaca cagcttggga gaccttgtct ccaaccatgc aagccaccat    4740
cgaagggctc aacgttgtgc actctgccac acgtgtgttc ggttccctct accaagcaca    4800
gaaccgtcgc ttcagcaaca cctcagtcaa ggtgatggat gttgatgctg gtgacagaga    4860
gacagtccat cccttggttg tgactcatcc tggctctgga aggaaaggcc tttatgtgaa    4920
tcaagtctac tgtcagagaa ttgagggcat gacagatgca gaatcaaagc cattgcttca    4980
gttcctctat gagcatgcca ccagatttga cttcacttgc cgtgtgaggt ggaagaaaga    5040
ccaagtcctt gtctgggaca acttgtgcac catgcaccgt gctgttcctg actatgctgg    5100
caagttcaga tacttgactc gcaccacagt tggtggagtt aggcctgccc gctgagtagt    5160
tagcttaatc acctagagct cgtttaaact gagggcactg aagtcgcttg acgtgctgaa    5220
ttgtttgtga tgttggtggc gtattttgtt taaataagta agcatggctg tgattttatc    5280
atatgatcga tctttggggt tttatttaac acattgtaaa atgtgtatct attaataact    5340
caatgtataa gatgtgttca ttcttcggtt gccatagatc tgcttatttg acctgtgatg    5400
ttttgactcc aaaaaccaaa atcacaactc aataaactca tggaatatgt ccacctgttt    5460
cttgaagagt tcatctacca ttccagttgg catttatcag tgttgcagcg cgctgtgct    5520
ttgtaacata acaattgtta cggcatatat ccaatagcgg ccggcctcct gcagggttta    5580
aacttgccgt ggcctatttt cagaagaagt tcccaatagt agtccaaaat ttttgtaacg    5640
aagggagcat aatagttaca tgcaaaggaa aactgccatt ctttagaggg gatgcttgtt    5700
taagaacaaa aaatatatca ctttcttttg ttccaagtca ttgcgtattt ttttaaaaat    5760
atttgttcct tcgtatattt cgagcttcaa tcactttatg gttctttgta ttctggcttt    5820
gctgtaaatc gtagctaacc ttcttcctag cagaaattat taatacttgg gatatttttt    5880
tagaatcaag taaattacat attaccacca catcgagctg cttttaaatt catattacag    5940
ccatataggc ttgattcatt ttgcaaaatt tccaggatat tgacaacgtt aacttaataa    6000
tatcttgaaa tattaaagct attatgatta ggggtgcaaa tggaccgagt tggttcggtt    6060
tatatcaaaa tcaaaccaaa ccaactatat cggtttggat tggttcggtt ttgccgggtt    6120
ttcagcattt tctggttttt ttttttgttag atgaatatta tttttaatctt actttgtcaa    6180
attttttgata agtaaatata tgtgttagta aaaattaatt ttttttacaa acatatgatc    6240
tattaaaata ttcttatagg agaattttct taataacaca tgatatttat ttattttagt    6300
cgtttgacta atttttcgtt gatgtacact ttcaaagtta accaaattta gtaattaagt    6360
ataaaaatca atatgatacc taaataatga tatgttctat ttaatttaa attatcgaaa    6420
tttcacttca aattcgaaaa agatatataa gaatttgat agattttgac atatgaatat    6480
ggaagaacaa agagattgac gcattttagt aacacttgat aagaaagtga tcgtacaacc    6540
aattatttaa agttaataaa aatggagcac ttcatattta acgaaatatt acatgccaga    6600
agagtcgcaa atatttctag atatttttta aagaaaattc tataaaaagt cttaaaggca    6660
tatatataaa aactatatat ttatattttt tacccaaaag caccgcaagg ggtagccctg    6720
```

```
ggtgtgcgga cggactctaa acaccgacag ctggcgcgcc aggtaggggg tgtgtctttg    6780
atctgagcta gctcaatgac cattacctcc aaatgcaaga tcgcccttcg ccccgggact    6840
atgttttgct ttggaaccat ctcatccata gcagatgaag agggaactct gcaccgcata    6900
gcagatctat tggagaagaa gctttcctca gaaatctcga ggggagccag ggcagaacag    6960
cgggtggcac catcacccgc acctcaagcg aagatgacct cttacaaacc gaaagtcggg    7020
agctcaccta cccgaaaaac tccgctgtcc acttcgccca caaggagtg gacacggatt    7080
actcgaaaga aggaagcgag tgtcccgagt caggggacgg gaacacgcca agccatcttt    7140
ccgacgcctt cgccctcaaa tgaggatgga aagaagagcg ccatcgcgct ggctcctttc    7200
taccccgacg tcctcttcat caggggggaga ttggagttag cacccgtctt caacgatgag    7260
ccaaccatgc aagggaaga gcctccccag cgtgaggcgc gacgacggag gaatagaagc    7320
cagaacgtgc ggcgacatca cgaggctggg gaacgggatc cggcgcaacc cgtatcccgg    7380
gacgaagctt tagaagtagg aaaaactccc gacgagtggg tacaccgaga aaggcggaac    7440
tctcgccgcc gtgatcgccg acaagcttag gaccgagaac gagagcaagc cgagcaaggt    7500
gcaaggctgc gccgagagaa tgctctcttt gctcggaacc tgtaccccga cttcgctcgt    7560
gcaatgaaca cgccgagtga agtcggaggg gtactggccc agatagctga cggcctcccg    7620
cgaaccctag acacggaagg ctaccggcgg ctgcttactc gagcagttaa tcaccttcta    7680
cccatcacta atcctccaag cgacctacgc catgccatca acagccggcg agacacgcgg    7740
agctccatca acgcttcgcg cgaccgatga cacgaaagtg agatagggaa ccgagaggag    7800
tatgtccgag atcatgccat cctggcatga agtcatgcca cccgagctga gtcggttgcg    7860
gcctcgacca gtgtcccgtt ccagggacga tcaagatgac acacaactgg ctcccctcct    7920
tgggaccgac ctcacgaacg ccgacatgaa gacacgtgcg gagtcttcgc acttactccg    7980
tgtctccggg ccatccagtg gcccctaact tcaaggtctc caacgtcagc aagtatgagc    8040
gcaagcagga cctgggtggc tggttagcca tctacacgat tgtcacatgg gccgccggag    8100
cgacggagga cgtgatgaca gtgtattttc ccattgtcct agggcaagac gcaatgcagt    8160
ggctccgaca tctaccccaa cattgcatag acaattggag cgacttcagt tggtgcttca    8220
tcgccaactt ccagtccctc tttgacaagc cggcgcagcc atgggaccta aaatccattg    8280
ggcatcaggg cgatgaaacg ctccggttgt acctcaagag gttttagacc atgaggaacc    8340
acaccccga agtcgccgag gcggggggtga ttgaagactt ctaccgagga tccaatgact    8400
cggctttcgt ccgagccata ctccagaaaa gcgtcggcca cctccgaaca cttgttccgg    8460
gaggcagacc tctacatcac cacggattaa cgggcccagg acctcatcgg aggcacgaaa    8520
gccgcgccac acgcgccacg gtgtgacacg aaccagc                            8557
```

CONTROL OF AAD-1 MONOCOT VOLUNTEERS IN FIELDS OF DICOT CROPS

CROSS REFERENCE TO RELATED APPLICATIONS

This application is a 371 national stage application of International Application No. PCT/US2010/045870, with an International Filing Date of Aug. 18, 2010, which claims priority to U.S. Application No. 61/235,248, filed on Aug. 19,2009, and to U.S. Application No. 61/328,944, filed on Aug. 28, 2010, all of which are incorporated herein by reference in their entirety.

BACKGROUND

Corn (monocot) and soybeans (dicot), for example, can be rotated in various crop rotation cycles in various geographies. Cotton is also a dicot.

"Volunteer" plants are unwanted plants from the prior growing season that emerge in a field planted with crops for the current growing season. Volunteers are basically weeds, and can, like weeds, reduce harvest and yield of the crop of interest for the current growing season. The volunteers divert fertilizer resources and the like from the desired crops.

Unlike plain weeds, volunteers are often specifically engineered to be resistant to some herbicides. Thus, controlling volunteers can be more difficult than controlling naturally occurring weeds.

AAD (aryloxy alkanoate dioxygenase) genes as described herein impart high levels of tolerance to 2,4-D herbicides in plants that are transformed with an AAD gene.

AAD-1 genes (encoding SEQ ID NO:1, SEQ ID NO:2, and SEQ ID NO:3, for example, of the attached sequence listing; see WO 2005 107437) also impart high levels of tolerance to phenoxy- and aryloxyphenoxyproplonate herbicides ("fops" such as fluazifop and haloxyfop) to corn and other monocot species transformed with the gene. (Fops are primarily used to control monocots, as dicots tend to have some natural resistance to fops.) Thus, AAD-1 allows the use of some fops as either selection agents or as herbicides on crops where crop destruction would be expected without the AAD-1 gene.

AAD-12 and AAD-13 genes also impart high levels of tolerance to pyridyloxyacetate herbicides (such as triclopyr and fluroxypyr; "pyrs"). Thus, AAD-12 and AAD-13 each allow the use of pyrs as either selection agents or as herbicides on crops where crop destruction would be expected without the AAD-12 or AAD-13 gene.

There are very numerous types of monocot- or grass-only herbicides (that kill monocots).

ACCase inhibitor herbicides include fops and dims.

BRIEF SUMMARY

The subject invention relates in part to the control of AAD-1 monocot volunteers in fields planted with dicot crops such as soybeans or cotton.

The subject invention also relates in part to the recognition that one potential downside to the use of AAD genes is that volunteers can be resistant to 2,4-D, as well as to fops (in the case of AAD-1). In the case of AAD-1, fop herbicides will no longer be effective for control of volunteer AAD-1 corn in fields planted with dicot crops such as soybean or cotton. The subject invention relates in part to the recognition that when an AAD gene is stacked with other herbicide resistance traits (such as glyphosate, glufosinate, and the like) in corn, control of volunteer corn plants in the following year can be an issue.

According to some embodiments of the subject invention, cyclohexanedione ('dim') herbicides (such as clethodim, sethoxydim, and the like) are selected, from almost innumerable other options, as being an effective tool for controlling AAD-1 'volunteers,' as AAD genes do not impart tolerance to this class of graminicide chemistry. Dims tend to be moncot-specific.

In addition, the following imidazolinone-class herbicides can be used, in some preferred embodiments, according to the subject invention: imazethapyr, imazamox, and imazaquin. Soy is naturally tolerant to these herbicides, so these imidazolinones can be used for selective control of conventional or herbicide-tolerant varieties of volunteer corn. (Non-commercialized CLEARFIELD cotton and imidazolinone-resistant soy was developed by BASF; cotton is not naturally tolerant to imidazolinones.)

This is assuming that the corn from the previous season was susceptible to imidazolinones. (Soybeans are naturally tolerant to certain imidazolinones.) Corn is generally susceptible to imidazolinones except for CLEARFIELD corn, which is tolerant to imidazolinones.

Use of other types of herbicides, including ALS—(acetolactate synthase) and/or AHAS—(acetohyroxyacid synthase) inhibitors could also be used according to the subject invention for the control of volunteer AAD monocot plants as well.

A third option, according to the subject invention, is to use other herbicides, as described herein, for controlling AAD-1 volunteers. These options include herbicides that provide a relatively fast "burn down," and non-selective herbicides, such as paraquat, used pre-plant.

AAD-1 corn comprising Event DAS-40278-9 is used in some particularly preferred embodiments.

BRIEF DESCRIPTION OF THE SEQUENCES

SEQ ID NO:1 is the native protein sequence encoded by the AAD-1 v1 gene from *Sphingobium herbicidivorans*.

SEQ ID NO:2 is the amino acid sequence encoded by the AAD-1 v2 gene, which removed an internal NotI restriction site.

SEQ ID NO:3 is the amino acid sequence encoded by the AAD-1 v3 gene, which has plant codon usage for expression in a plant.

SEQ ID NO:4 is a sequence for corn Event DAS-40278-9, which includes 5' and 3' corn genomic flanking sequences, and the AAD-1 cassette insert sequence.

DETAILED DESCRIPTION

As used herein and unless otherwise specified, preferred dicots are soybeans or cotton.

ACCase inhibitor herbicides include fops and dims.

One aspect of the subject invention includes the use of 'dim' herbicides to remove volunteer AAD-1 corn in fields of dicots. In some specific embodiments, the AAD-1 gene is present in the corn as the AAD-1 corn event designated DAS-40278-9 having seed deposited with American Type Culture Collection (ATCC) with Accession No. PTA-10244 (Yellow Dent maize hybrid seed (*Zea Mays* L.):DAS-40278-9; Deposited in accordance with the Budapest Treaty on behalf of Dow AgroSciences LLC; Date of receipt of seeds/strain(s) by the ATTC: Jul. 10, 2009; viability confirmed Aug. 17, 2009), and progeny derived thereof. See also SEQ ID NO:4. This event is disclosed in U.S. Ser. No. 61/235,248 (filed Aug. 19, 2009). Such AAD-1 monocot volunteers could be present in the following year's soybeans, cotton, or other broadleaf crop. Thus, the subject invention includes the application of a dim (or other as disclosed herein) herbicide to volunteer AAD-1 corn plants, particularly where the corn plant comprises the 40278-9 event.

Because of the specific detoxifying aspects of AAD genes, 'dim' herbicides would not be subject to detoxification by AAD-1, and AAD-1 monocot volunteers would remain highly susceptible to dim herbicides. Thus, the subject invention includes the use of one or more dim herbicides, where the AAD-1 gene was used alone or stacked with other herbicide tolerance traits.

In some other preferred embodiments, imidazolinones can be used according to the subject invention to control monocot/corn volunteers in dicot fields. If the corn was susceptible to an imidazolinone and the dicots are resistant to imidazolinones, then a "dim" and/or imidazolinone herbicide could be used in the dicot fields to control the AAD-1 corn volunteers. However, if CLEARFIELD corn (which is resistant to imidazolinones), for example, was planted in the previous season, this would tend to preclude the use of imidazolinones the following season to control corn volunteers in dicot fields.

As alluded to above, selection of herbicides to use on the current planted fields, according to the subject invention, depends in part on the herbicide-tolerant trait(s) that are present in both the volunteers (the monocot crop of the prior season), if any, and the herbicide resistance trait(s) that are present in the field of dicot crops of the current growing season. Thus, additional herbicide chemistries can be selected to provide control of AAD-1 corn depending on the stack, if any, with other herbicide tolerant traits in the corn, and on the tolerance or susceptibility of the dicot (soybeans or cotton) in the field to be treated.

For example, if the volunteer AAD-1 corn was also stacked with a glyphosate- or glufosinate-trait, then glufosinate or glyphosate, respectively, could be used in the soybean field of the current season, assuming that the soybeans also have a resistance trait against glufosinate or glyphosate, respectively.

If the volunteer AAD-1 corn was also stacked with a glyphosate- and glufosinate-traits, then dims and/or imidazolinones could still be used in the soybean fields to control the AAD-1 corn volunteers (again assuming that the corn does not have a resistance trait against an imidazolinone if an imidazolinone is used to control the volunteers).

When an AAD-1 gene was used alone in corn in the previous growing season, imidazolinone, "dims," glyphosate, and/or glufosinate could be used the following season to control the volunteer AAD-1 corn in planted fields of soybean or cotton that, assuming that the dicots are tolerant/resistant to any one or more of these further herbicides (such as glyphosate and/or glufosinate). That is, glyphosate and/or glufosinate could be used if the soybeans or cotton are engineered or bred to be tolerant to glyphosate and/or glufosinate, respectively.

When an AAD-1 gene was stacked in corn with, for example, a glyphosate or glufosinate resistant trait (such as is found in Roundup Ready [or GAT or other glyphosate-tolerant crops] or Liberty Link [or other glufosinate-tolerant] corn), then imidazolinone and/or a "dim" herbicide could be used to control volunteer AAD-1 corn in the dicot crops (assuming the dicot crop is resistant to imidazolinone if an imidazolinone herbicide is to be used).

Glufosinate or glyphosate, respectively, could also be used, assuming that the dicot crops are resistant to that herbicide and the corn is susceptible. That is, if the soybeans have a trait for glyphosate tolerance but not glufosinate tolerance, for example, then glyphosate could also be used (assuming ROUNDUP READY corn is not the volunteers). If the soybeans have a glufosinate tolerance trait (such as PAT) but not a glyphosate tolerance trait, then glufosinate could also be used (assuming that LIBERTY LINK corn is not the volunteers).

In any of those stacking scenarios (and even if AAD-1, glyphosate tolerance, and glufosinate tolerance, and imidazolinone tolerance traits were all present in the corn of the previous season), dims could be used in the soybean fields to control the AAD-1 corn volunteers.

In some embodiments, AAD-1 monocot volunteers can be controlled, using combinations of herbicides disclosed herein—see Examples 4 and 5, in fields of monocots. These embodiments include control of AAD-1 Event DAS-40278-9 corn volunteers in fields of monocots. Such embodiments include turf-in-turf (AAD-1 turf volunteers in a field of other (non-AAD1) turf.

EXAMPLES

Example 1

Control of Volunteer AAD Maize in a Field Planted with Soybean Using Alternative Herbicides In one embodiment, volunteer transgenic maize lines containing an AAD expression cassette (AAD-1) are controlled within a field of soybean by the application of a herbicide or combination of herbicides. The specific herbicide used to control the volunteer transgenic AAD maize line is dependent upon the type of soybean seed being planted within the field (e.g., conventional soybean, Round-up Ready Soybean, Liberty Link Soybean, etc.).

Furthermore, the AAD trait may be stacked with other additional herbicide tolerant trait(s) via conventional breeding or a molecular stack. In such an example, the specific herbicide used to control the volunteer AAD maize stacked with another herbicide tolerant trait(s) will be dependent upon the additional herbicide tolerant trait(s) and the type of soybean being planted within the field.

The application of a given herbicide can be made before planting at pre-emergence/burndown or post-emergence after planting to control the volunteer transgenic AAD maize lines. Table 1 lists the herbicides to be used at the different stages of planting (pre-emergence or post-emergence) to control volunteer transgenic AAD maize. At or about a 1× Field Rate concentration of herbicide would be applied, as either a tank mix or alone, to the field for both pre-emergent and post-emergent volunteer control.

The control of transgenic maize plants containing the AAD expression cassette within a field of soybean would be applicable for the control of volunteer AAD transgenic monocot plants (including, but not limited too; corn, rice, sugar cane, switch grass, turf grass species, sorghum, barley, wheat, and oats, and durum) within a field being planted with a dicot crop (including, but not limited too; soybean, cotton, canola, flax, sunflower, legumes, alfalfa, peanut, and tomato). The example described above, in which volunteer transgenic AAD maize plants are controlled in a soybean field, is illustrative of the invention and not intended to restrict the scope of this embodiment.

Example 2

Control of Volunteer Corn (Conventional or Containing Non-AAD Herbicide Tolerance Traits) in a Field Planted with AAD Soybean Using Alternative Herbicides In an embodiment, volunteer transgenic corn lines (containing the Clear Field trait, Roundup Ready or other Glyphosate Tolerant Trait, Liberty Link Trait, Imidazolonine tolerant trait, or any stacked combination thereof) or volunteer conventional corn lines are controlled within a field of transgenic AAD soybean (AAD-12) by the application of a herbicide or combination of herbicides. The specific herbicide used to control the volunteer corn plants is dependent upon the type of corn seed being planted within the field (e.g., conventional soybean, Round-up Ready Soybean, Liberty Link Soybean, etc.). Additionally, the specific herbicide used to control the volunteer conventional or transgenic corn line is dependent upon the type of AAD transgenic soybean seed (i.e. stacked traits or alone) being planted within the field and the trait possessed by the volunteer corn line.

The application of a given herbicide can be made before planting at pre-emergence/burndown or post-emergence after planting to control the volunteer conventional or transgenic soybean lines. Table 2 and Table 3 list the herbicides to be used at the different stages of planting (pre-emergence or post-emergence) to control volunteer conventional or transgenic corn. At or about a 1× Field Rate concentration of herbicide would be applied, as either a tank mix or alone, to the field for both pre-emergent and post-emergent volunteer control.

The control of conventional or transgenic corn plants containing a herbicide tolerant expression cassette within a field of AAD transgenic soybean (either stacked with other herbicide tolerant traits or alone) would be applicable for the control of a conventional or herbicide tolerant transgenic monocot plant (including, but not limited too; corn, rice, sugar cane, switch grass, turf grass species, sorghum, barley, wheat, and oats, and durum) within a field being planted with an AAD transgenic dicot crop (including, but not limited too; soybean, cotton, canola, flax, sunflower, legumes, alfalfa, peanut, and tomato). The example described above, in which volunteer conventional or transgenic herbicide tolerant corn plants are controlled in a field planted with AAD transgenic soybean, is illustrative of the invention and not intended to restrict the scope of this embodiment.

Example 3

Control of Volunteer AAD-1 Maize in a Field Planted with AAD-12 Cotton Using Alternative Herbicides In one embodiment, volunteer transgenic maize lines containing an AAD-1 expression cassette are controlled within a field of AAD-12 cotton by the application of a herbicide or combination of herbicides. The specific herbicide used to control the volunteer transgenic AAD-1 maize line is dependent upon the type of AAD-12 cotton seed being planted within the field (e.g., AAD-12 cotton or AAD-12 cotton stacked with Round-up Ready, Liberty Link, or other herbicide tolerant traits).

Furthermore, the AAD-1 trait may be stacked with other additional herbicide tolerant trait(s) via conventional breeding or a molecular stack. In such an example, the specific herbicide used to control the volunteer AAD-1 maize stacked with another herbicide tolerant trait(s) will be dependent upon the additional herbicide tolerant trait(s) and the type of cotton being planted within the field.

The application of a given herbicide can be made before planting at pre-emergence/burndown or post-emergence after planting to control the volunteer transgenic AAD-1 maize lines. Table 4 lists the herbicides to be used at the different stages of planting (pre-emergence or post-emergence) to control volunteer transgenic AAD-1 maize. At or about a 1× Field Rate concentration of herbicide would be applied, as either a tank mix or alone, to the field for both pre-emergent and post-emergent volunteer control.

The control of transgenic maize plants containing the AAD-1 expression cassette within a field of AAD-12 cotton would be applicable for the control of volunteer AAD-1 transgenic monocot plants (including, but not limited too; corn, rice, sugar cane, switch grass, turf grass species, sorghum, barley, wheat, and oats, and durum) within a field being planted with an AAD-12 dicot crop (including, but not limited too; soybean, cotton, canola, flax, sunflower, legumes, alfalfa, peanut, and tomato). The example described above, in which volunteer transgenic AAD-1 maize plants are controlled in an AAD-12 cotton field, is illustrative of the invention and not intended to restrict the scope of this embodiment.

TABLE 1

Control of volunteer AAD-1 (trait alone or stacked with other HT traits) corn (or other monocot) in soybean (or other dicot crops)

| Previous year Corn hybrid | Current year Soybean variety being planted | Herbicides option - Burndown/PRE | Herbicides option - POST |
|---|---|---|---|
| Application: alone and tank mixes | | | |
| AAD-1 | Soybean, conventional | Glyphosate, Dims, IMI, glufosinate, paraquat, other ALS herbicides not recommended for corn (need to be aware of planting restrictions) enabled by "ALS gene" | Dims, IMI |
|  | RR Soybean |  | Dims, Glyphosate, IMI |
|  | LL Soybean |  | Dims, Glufosinate, IMI |
|  | GAT + ALS |  | Dims, IMI, ALS inhibitors not selective for in-corn application |
|  | AAD-12 |  | Dims, IMI |
|  | AAD-12 + GT |  | Dims, Glyphosate, IMI |
|  | AAD-12 + PAT |  | Dims, Glufosinate, IMI |
|  | AAD-12 + AHAS |  | Dims, IMI |
|  | AAD-12 + PAT + GT |  | Dims, Glyphosate, glufosinate, IMI |
|  | AAD-12 + PAT + AHAS |  | Dims, glufosinate, IMI |
|  | AAD-12 + GAT |  | Dims, IMI, glyphosate, ALS inhibitors not selective for in-corn application |
|  | AAD-12 + PAT + GAT |  | Dims, IMI, glufosinate glyphosate, ALS inhibitors not selective for in-corn application |

TABLE 1-continued

Control of volunteer AAD-1 (trait alone or stacked with other HT traits) corn (or other monocot) in soybean (or other dicot crops)

| Previous year Corn hybrid | Current year Soybean variety being planted | Herbicides option - Burndown/PRE | Herbicides option - POST |
|---|---|---|---|
| AAD-1 + PAT | Soybean, conventional | Glyphosate, Dims, IMI, paraquat, other ALS herbicides not recommended for corn (need to be aware of planting restrictions) enabled by "ALS gene" | Dims, IMI |
| | RR Soybean | | Dims, Glyphosate, IMI |
| | LL Soybean | | Dims, IMI |
| | GAT | | Dims, IMI, ALS inhibitors not selective for in-corn application |
| | AAD-12 | | Dims, IMI |
| | AAD-12 + GT | | Dims, Glyphosate, IMI |
| | AAD-12 + PAT | | Dims, IMI |
| | AAD-12 + AHAS | | Dims, IMI |
| | AAD-12 + PAT + GT | | Dims, Glyphosate, IMI |
| | AAD-12 + PAT + AHAS | | Dims, IMI |
| | AAD-12 + GAT | | Dims, IMI, glyphosate, ALS inhibitors not selective for in-corn application |
| | AAD-12 + PAT + GAT | | Dims, IMI, glyphosate, ALS inhibitors not selective for in-corn application |
| AAD-1 + GT | Soybean, conventional | Dims, IMI, glufosinate, paraquat, other ALS herbicides not recommended for corn (need to be aware of planting restrictions) enabled by "ALS gene" | Dims, IMI |
| | RR Soybean | | Dims, IMI |
| | LL Soybean | | Dims, Glufosinate IMI |
| | GAT | | Dims, IMI, ALS inhibitors not selective for in-corn application |
| | AAD-12 | | Dims, IMI |
| | AAD-12 + GT | | Dims, IMI |
| | AAD-12 + PAT | | Dims, Glufosinate, IMI |
| | AAD-12 + AHAS | | Dims, IMI |
| | AAD-12 + PAT + GT | | Dims, glufosinate, IMI |
| | AAD-12 + PAT + AHAS | | Dims, glufosinate, IMI |
| | AAD-12 + GAT | | Dims, IMI, ALS inhibitors not selective for in-corn application |
| | AAD-12 + PAT + GAT | | Dims, IMI, glufosinate, ALS inhibitors not selective for in-corn application |
| AAD-1 + AHAS | Soybean, conventional | Glyphosate, Dims, glufosinate, paraquat, other ALS herbicides not recommended for corn (need to be aware of planting restrictions) enabled by "ALS gene" | Dims |
| | RR Soybean | | Dims, Glyphosate |
| | LL Soybean | | Dims, Glufosinate |
| | GAT | | Dims, ALS inhibitors not selective for in-corn application |
| | AAD-12 | | Dims |
| | AAD-12 + GT | | Dims, Glyphosate |
| | AAD-12 + PAT | | Dims, Glufosinate |
| | AAD-12 + AHAS | | Dims |
| | AAD-12 + PAT + GT | | Dims, Glyphosate, glufosinate |
| | AAD-12 + PAT + AHAS | | Dims, glufosinate |
| | AAD-12 + GAT | | Dims, glyphosate, ALS inhibitors not selective for in-corn application |
| | AAD-12 + PAT + GAT | | Dims, glufosinate glyphosate, ALS inhibitors not selective for in-corn application |
| AAD-1 + PAT + GT | Soybean, conventional | Dims, IMI, paraquat, other ALS herbicides not recommended for corn (need to be aware of planting restrictions) enabled by "ALS gene" | Dims, IMI |
| | RR Soybean | | Dims, IMI |
| | LL Soybean | | Dims, Glufosinate, IMI |
| | GAT | | Dims, IMI, ALS inhibitors not selective for in-corn application |
| | AAD-12 | | Dims, IMI |
| | AAD-12 + GT | | Dims, IMI |
| | AAD-12 + PAT | | Dims, IMI |
| | AAD-12 + AHAS | | Dims, IMI |
| | AAD-12 + PAT + GT | | Dims, IMI |
| | AAD-12 + PAT + AHAS | | Dims, IMI |
| | AAD-12 + GAT | | Dims, IMI, ALS inhibitors not selective for in-corn application |
| | AAD-12 + PAT + GAT | | Dims, IMI, ALS inhibitors not selective for in-corn application |

TABLE 1-continued

Control of volunteer AAD-1 (trait alone or stacked with other HT traits) corn (or other monocot) in soybean (or other dicot crops)

| Previous year Corn hybrid | Current year Soybean variety being planted | Herbicides option - Burndown/PRE | Herbicides option - POST |
|---|---|---|---|
| AAD-1 + PAT + AHAS | Soybean, conventional | Glyphosate, Dims, paraquat, other ALS herbicides not recommended for corn (need to be aware of planting restrictions) enabled by "ALS gene" | Dims |
|  | RR Soybean |  | Dims, Glyphosate |
|  | LL Soybean |  | Dims |
|  | GAT |  | Dims, glyphosate, ALS inhibitors not selective for in-corn application |
|  | AAD-12 |  | Dims |
|  | AAD-12 + GT |  | Dims, Glyphosate |
|  | AAD-12 + PAT |  | Dims |
|  | AAD-12 + AHAS |  | Dims |
|  | AAD-12 + PAT + GT |  | Dims, Glyphosate |
|  | AAD-12 + PAT + AHAS |  | Dims |
|  | AAD-12 + GAT |  | Dims |
|  | AAD-12 + PAT + GAT |  | Dims, glyphosate, ALS inhibitors not selective for in-corn application |
| AAD-1 + GAT + ALS | Soybean, conventional | Dims, glufosinate, paraquat, other ALS herbicides not recommended for corn (need to be aware of planting restrictions) enabled by "ALS gene" | Dims |
|  | RR Soybean |  | Dims |
|  | LL Soybean |  | Dims, Glufosinate |
|  | GAT + ALS |  | Dims |
|  | AAD-12 |  | Dims |
|  | AAD-12 + GT |  | Dims |
|  | AAD-12 + PAT |  | Dims, Glufosinate |
|  | AAD-12 + AHAS |  | Dims |
|  | AAD-12 + PAT + GT |  | Dims, Glufosinate |
|  | AAD-12 + PAT + AHAS |  | Dims, Glufosinate |
|  | AAD-12 + GAT |  | Dims |
|  | AAD-12 + PAT + GAT |  | Dims, Glufosinate |
| AAD-1 + PAT + GAT + ALS | Soybean, conventional | Dims, paraquat, other ALS herbicides not recommended for corn (need to be aware of planting restrictions) enabled by "ALS gene" | Dims |
|  | RR Soybean |  | Dims |
|  | LL Soybean |  | Dims |
|  | GAT + ALS |  | Dims |
|  | AAD-12 |  | Dims |
|  | AAD-12 + GT |  | Dims |
|  | AAD-12 + PAT |  | Dims |
|  | AAD-12 + AHAS |  | Dims |
|  | AAD-12 + PAT + GT |  | Dims |
|  | AAD-12 + PAT + AHAS |  | Dims |
|  | AAD-12 + GAT |  | Dims |
|  | AAD-12 + PAT + GAT |  | Dims |

Gene and trait footnotes:

GT = any glyphosate specific tolerance trait including Roundup Ready (CP4), TIPS EPSPS (GA21, Glytol, DMMG), Athenix's EPSPS, GAT only without ALS, GOX, glyphosate decarboxylase, etc.

ALS = double mutant ALS gene insensitive to all ALS herbicide chemistries including IMI herbicides.

AAD-1 = Aryloxyalkanoate dioxygenase gene providing tolerance to all commercial phenoxy auxin and all aryloxyphenoxypropionate (fop) herbicides.

AAD-12 = Aryloxyalkanoate dioxygenase gene providing tolerance to phenoxyacetic auxin and pyridyloxyacetic auxin herbicides.

PAT = phosphinothricin acetyltransferase gene providing tolerance to glutamine synthetase inhibitors including, but not limited to, glufosinate. Similar phenotype is provided by genes such as BAR, DSM1, DSM2, et al.

AHAS = imidazolonine specific tolerance gene associated with point mutation at S623 of ALS gene (maize sequence) or equivalent amino acid in other spp (e.g., S653 in *Arabidopsis*).

RR = Roundup Ready trait, implies utility of CP4 gene as commercially deployed either alone or in combination with other genes but imparting glyphosate only tolerance.

CL = Clearfield crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.

LL = Liberty Link trait, implies utility of either PAT or BAR gene as commercially deployed either alone or in combination with other genes but imparting only tolerance to glutamine synthetase inhibitors such as glufosinate.

STS = designates resistance to sulfonylurea herbicide chemistry with use of ALS1 gene.

Herbicide footnotes:

IMI = any imidazolinone herbicide including, but not limited to, imazapyr, imazethapyr, imazamox, imazaquin.

DIMS = cyclohexanedione class of herbicides (dims) including, but not limited to, sethoxydim, clethodim, and for the purposes of this demonstration poinoxaden.

Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.

ALS inhibitors = any ALS inhibitor to the exclusion of IMI's for the sake of this demonstration (i.e., sulfonylureas, triazolopyrimidine sulfonanalides, sulfonylaminocarbonyltriazolinone).

HPPD = p-Hydroxyphenyl pyruvate dioxygenase inhibitor class of chemistry including but not limited to mesotrione, sulcotrione, isoxaflutole, and pyrazolynate.

MSMA and DSMA = herbicides from the organoarsenicals chemistry family.

N/A = No suitable options available postemergence.

TABLE 2

Control of volunteer corn (or other monocot) [trait alone or stacked with other HT traits] in AAD-1 Soybean or other dicot crops)

| Previous year Corn hybrid (or other monocot) | Current year Soybean variety (or other dicot) being planted | Herbicides option - Burndown/PRE | Herbicides option - POST |
|---|---|---|---|
| | | Appl: alone and tank mixes | |
| Conventional corn | AAD-1 | Glufosinate, Glyphosate, Fops, Dims, IMI, Paraquat, 2,4-D, Dichlorprop, MCPA, MCPP (Mecoprop), Dicamba, HPPD not recommended for corn other ALS herbicides not recommended for corn (need to be aware of planting restrictions) enabled by "ALS gene" | 2,4-D, Dichloprop, Fops, MCPA, MCPP (Mecoprop), Dims, IMI |
| | AAD-1 + GT | | 2,4-D, Dichloprop, Fops, MCPA, MCPP (Mecoprop), Dims, Glyphosate, IMI |
| | AAD-1 + PAT | | 2,4-D, Dichloprop, Fops, MCPA, MCPP (Mecoprop), Dims, Glufosinate, IMI |
| | AAD-1 + AHAS | | 2,4-D, Dichloprop, Fops, MCPA, MCPP (Mecoprop), Dims, IMI |
| | AAD-1 + PAT + GT | | 2,4-D, Dichloprop, Fops, MCPA, MCPP (Mecoprop), Dims, Glufosinate, Glyphosate, IMI |
| | AAD-1 + PAT + AHAS | | 2,4-D, Dichloprop, Fops, MCPA, MCPP (Mecoprop), Dims, Glufosinate, IMI |
| | AAD-1 + GAT + ALS | | 2,4-D, Dichloprop, Fops, MCPA, MCPP (Mecoprop), Dims, Glyphosate, IMI, ALS inhibitors not selective for in-corn application |
| | AAD-1 + PAT + GAT + ALS | | 2,4-D, Dichloprop, Fops, MCPA, MCPP (Mecoprop), Dims, Glufosinate, Glyphosate, IMI, ALS inhibitors not selective for in-corn application |
| CL Corn | AAD-1 | Glufosinate, Glyphosate, Fops, Dims, Paraquat, 2,4-D, Dichlorprop, MCPA, MCPP (Mecoprop), Dicamba, HPPD not recommended for corn other ALS herbicides not recommended for corn (need to be aware of planting restrictions) enabled by "ALS gene" | 2,4-D, Dichloprop, Fops, MCPA, MCPP (Mecoprop), Dims |
| | AAD-1 + GT | | 2,4-D, Dichloprop, Fops, MCPA, MCPP (Mecoprop), Dims, Glyphosate, |
| | AAD-1 + PAT | | 2,4-D, Dichloprop, Fops, MCPA, MCPP (Mecoprop), Dims, Glufosinate, |
| | AAD-1 + AHAS | | 2,4-D, Dichloprop, Fops, MCPA, MCPP (Mecoprop), Dims, |
| | AAD-1 + PAT + GT | | 2,4-D, Dichloprop, Fops, MCPA, MCPP (Mecoprop), Dims, Glufosinate, Glyphosate, |
| | AAD-1 + PAT + AHAS | | 2,4-D, Dichloprop, Fops, MCPA, MCPP (Mecoprop), Dims, Glufosinate, |
| | AAD-1 + GAT + ALS | | 2,4-D, Dichloprop, Fops, MCPA, MCPP (Mecoprop), Dims, Glyphosate, ALS inhibitors not selective for in-corn application |
| | AAD-1 + PAT + GAT + ALS | | 2,4-D, Dichloprop, Fops, MCPA, MCPP (Mecoprop), Dims, Glufosinate, Glyphosate, ALS inhibitors not selective for in-corn application |

TABLE 2-continued

Control of volunteer corn (or other monocot) [trait alone or stacked with other HT traits] in AAD-1 Soybean or other dicot crops)

| Previous year Corn hybrid (or other monocot) | Current year Soybean variety (or other dicot) being planted | Herbicides option - Burndown/PRE | Herbicides option - POST |
|---|---|---|---|
| RR or GT Corn | AAD-1 | Glufosinate, Fops, Dims, IMI, Paraquat, 2,4-D, Dichlorprop, MCPA, MCPP (Mecoprop), Dicamba, HPPD not recommended for corn other ALS herbicides not recommended for corn (need to be aware of planting restrictions) enabled by "ALS gene" | 2,4-D, Dichloprop, Fops, MCPA, MCPP (Mecoprop), Dims, IMI |
| | AAD-1 + GT | | 2,4-D, Dichloprop, Fops, MCPA, MCPP (Mecoprop), Dims, IMI |
| | AAD-1 + PAT | | 2,4-D, Dichloprop, Fops, MCPA, MCPP (Mecoprop), Dims, Glufosinate, IMI |
| | AAD-1 + AHAS | | 2,4-D, Dichloprop, Fops, MCPA, MCPP (Mecoprop), Dims, IMI |
| | AAD-1 + PAT + GT | | 2,4-D, Dichloprop, Fops, MCPA, MCPP (Mecoprop), Dims, Glufosinate, IMI |
| | AAD-1 + PAT + AHAS | | 2,4-D, Dichloprop, Fops, MCPA, MCPP (Mecoprop), Dims, Glufosinate, IMI |
| | AAD-1 + GAT + ALS | | 2,4-D, Dichloprop, Fops, MCPA, MCPP (Mecoprop), Dims, IMI, ALS inhibitors not selective for in-corn application |
| | AAD-1 + PAT + GAT + ALS | | 2,4-D, Dichloprop, Fops, MCPA, MCPP (Mecoprop), Dims, Glufosinate, IMI, ALS inhibitors not selective for in-corn application |
| LL Corn | AAD-1 | , Glyphosate, Fops, Dims, IMI, Paraquat, 2,4-D, Dichlorprop, MCPA, MCPP (Mecoprop), Dicamba, HPPD not recommended for corn other ALS herbicides not recommended for corn (need to be aware of planting restrictions) enabled by "ALS gene" | 2,4-D, Dichloprop, Fops, MCPA, MCPP (Mecoprop), Dims, IMI |
| | AAD-1 + GT | | 2,4-D, Dichloprop, Fops, MCPA, MCPP (Mecoprop), Dims, Glyphosate, IMI |
| | AAD-1 + PAT | | 2,4-D, Dichloprop, Fops, MCPA, MCPP (Mecoprop), Dims,, IMI |
| | AAD-1 + AHAS | | 2,4-D, Dichloprop, Fops, MCPA, MCPP (Mecoprop), Dims, IMI |
| | AAD-1 + PAT + GT | | 2,4-D, Dichloprop, Fops, MCPA, MCPP (Mecoprop), Dims,, Glyphosate, IMI |
| | AAD-1 + PAT + AHAS | | 2,4-D, Dichloprop, Fops, MCPA, MCPP (Mecoprop), Dims,, IMI |
| | AAD-1 + GAT + ALS | | 2,4-D, Dichloprop, Fops, MCPA, MCPP (Mecoprop), Dims, Glyphosate, IMI, ALS inhibitors not selective for in-corn application |
| | AAD-1 + PAT + GAT + ALS | | 2,4-D, Dichloprop, Fops, MCPA, MCPP (Mecoprop), Dims,, Glyphosate, IMI, ALS inhibitors not selective for in-corn application |
| GAT + ALS | AAD-1 | Glufosinate, Fops, Dims, Paraquat, 2,4-D, Dichlorprop, MCPA, MCPP (Mecoprop), Dicamba, HPPD not recommended for corn | 2,4-D, Dichloprop, Fops, MCPA, MCPP (Mecoprop), Dims |
| | AAD-1 + GT | | 2,4-D, Dichloprop, Fops, MCPA, MCPP (Mecoprop), Dims,, |
| | AAD-1 + PAT | | 2,4-D, Dichloprop, Fops, MCPA, MCPP (Mecoprop), Dims, Glufosinate |
| | AAD-1 + AHAS | | 2,4-D, Dichloprop, Fops, MCPA, MCPP (Mecoprop), Dims |
| | AAD-1 + PAT + GT | | 2,4-D, Dichloprop, Fops, MCPA, MCPP (Mecoprop), Dims, Glufosinate |

TABLE 2-continued

Control of volunteer corn (or other monocot) [trait alone or stacked with other HT traits] in AAD-1 Soybean or other dicot crops)

| Previous year Corn hybrid (or other monocot) | Current year Soybean variety (or other dicot) being planted | Herbicides option - Burndown/PRE | Herbicides option - POST |
|---|---|---|---|
| | AAD-1 + PAT + AHAS | | 2,4-D, Dichloprop, Fops, MCPA, MCPP (Mecoprop), Dims, Glufosinate |
| | AAD-1 + GAT + ALS | | 2,4-D, Dichloprop, Fops, MCPA, MCPP (Mecoprop), Dims |
| | AAD-1 + PAT + GAT + ALS | | 2,4-D, Dichloprop, Fops, MCPA, MCPP (Mecoprop), Dims, Glufosinate |
| CL (or AHAS) + PAT | AAD-1 | Glyphosate, Fops, Dims,, Paraquat, 2,4-D, Dichlorprop, MCPA, MCPP (Mecoprop), Dicamba, HPPD not recommended for corn other ALS herbicides not recommended for corn (need to be aware of planting restrictions) enabled by "ALS gene" | 2,4-D, Dichloprop, Fops, MCPA, MCPP (Mecoprop), Dims |
| | AAD-1 + GT | | 2,4-D, Dichloprop, Fops, MCPA, MCPP (Mecoprop), Dims, Glyphosate |
| | AAD-1 + PAT | | 2,4-D, Dichloprop, Fops, MCPA, MCPP (Mecoprop), Dims, |
| | AAD-1 + AHAS | | 2,4-D, Dichloprop, Fops, MCPA, MCPP (Mecoprop), Dims |
| | AAD-1 + PAT + GT | | 2,4-D, Dichloprop, Fops, MCPA, MCPP (Mecoprop), Dims, Glyphosate |
| | AAD-1 + PAT + AHAS | | 2,4-D, Dichloprop, Fops, MCPA, MCPP (Mecoprop), Dims |
| | AAD-1 + GAT + ALS | | 2,4-D, Dichloprop, Fops, MCPA, MCPP (Mecoprop), Dims, Glyphosate, ALS inhibitors not selective for in-corn application |
| | AAD-1 + PAT + GAT + ALS | | 2,4-D, Dichloprop, Fops, MCPA, MCPP (Mecoprop), Dims, Glyphosate, ALS inhibitors not selective for in-corn application |
| CL (or AHAS) + GT | AAD-1 | Glufosinate, Fops, Dims,, Paraquat, 2,4-D, Dichlorprop, MCPA, MCPP (Mecoprop), Dicamba, HPPD not recommended for corn other ALS herbicides not recommended for corn (need to be aware of planting restrictions) enabled by "ALS gene" | 2,4-D, Dichloprop, Fops, MCPA, MCPP (Mecoprop), Dims |
| | AAD-1 + GT | | 2,4-D, Dichloprop, Fops, MCPA, MCPP (Mecoprop), Dims, Glufosinate |
| | AAD-1 + PAT | | 2,4-D, Dichloprop, Fops, MCPA, MCPP (Mecoprop), Dims, |
| | AAD-1 + AHAS | | 2,4-D, Dichloprop, Fops, MCPA, MCPP (Mecoprop), Dims |
| | AAD-1 + PAT + GT | | 2,4-D, Dichloprop, Fops, MCPA, MCPP (Mecoprop), Dims, Glufosinate |
| | AAD-1 + PAT + AHAS | | 2,4-D, Dichloprop, Fops, MCPA, MCPP (Mecoprop), Dims |
| | AAD-1 + GAT + ALS | | 2,4-D, Dichloprop, Fops, MCPA, MCPP (Mecoprop), Dims, Glufosinate, ALS inhibitors not selective for in-corn application |
| | AAD-1 + PAT + GAT + ALS | | 2,4-D, Dichloprop, Fops, MCPA, MCPP (Mecoprop), Dims, Glufosinate, ALS inhibitors not selective for in-corn application |

TABLE 2-continued

Control of volunteer corn (or other monocot) [trait alone or stacked with other HT traits] in AAD-1 Soybean or other dicot crops)

| Previous year Corn hybrid (or other monocot) | Current year Soybean variety (or other dicot) being planted | Herbicides option - Burndown/PRE | Herbicides option - POST |
|---|---|---|---|
| GT + PAT | AAD-1 | Fops, Dims, IMI, Paraquat, 2,4-D, Dichlorprop, MCPA, MCPP (Mecoprop), Dicamba, HPPD not recommended for corn other ALS herbicides not recommended for corn (need to be aware of planting restrictions) enabled by "ALS gene" | 2,4-D, Dichloprop, Fops, MCPA, MCPP (Mecoprop), Dims, IMI |
| | AAD-1 + GT | | 2,4-D, Dichloprop, Fops, MCPA, MCPP (Mecoprop), Dims, IMI |
| | AAD-1 + PAT | | 2,4-D, Dichloprop, Fops, MCPA, MCPP (Mecoprop), Dims, IMI |
| | AAD-1 + AHAS | | 2,4-D, Dichloprop, Fops, MCPA, MCPP (Mecoprop), Dims, IMI |
| | AAD-1 + PAT + GT | | 2,4-D, Dichloprop, Fops, MCPA, MCPP (Mecoprop), Dims, IMI |
| | AAD-1 + PAT + AHAS | | 2,4-D, Dichloprop, Fops, MCPA, MCPP (Mecoprop), Dims, IMI |
| | AAD-1 + GAT + ALS | | 2,4-D, Dichloprop, Fops, MCPA, MCPP (Mecoprop), Dims, IMI, ALS inhibitors not selective for in-corn application |
| | AAD-1 + PAT + GAT + ALS | | 2,4-D, Dichloprop, Fops, MCPA, MCPP (Mecoprop), Dims, IMI, ALS inhibitors not selective for in-corn application |
| GT + CL (or AHAS) + PAT | AAD-1 | Fops, Dims, Paraquat, 2,4-D, Dichlorprop, MCPA, MCPP (Mecoprop), Dicamba, HPPD not recommended for corn other ALS herbicides not recommended for corn (need to be aware of planting restrictions) enabled by "ALS gene" | 2,4-D, Dichloprop, Fops, MCPA, MCPP (Mecoprop), Dims |
| | AAD-1 + GT | | 2,4-D, Dichloprop, Fops, MCPA, MCPP (Mecoprop), Dims |
| | AAD-1 + PAT | | 2,4-D, Dichloprop, Fops, MCPA, MCPP (Mecoprop), Dims |
| | AAD-1 + AHAS | | 2,4-D, Dichloprop, Fops, MCPA, MCPP (Mecoprop), Dims |
| | AAD-1 + PAT + GT | | 2,4-D, Dichloprop, Fops, MCPA, MCPP (Mecoprop), Dims |
| | AAD-1 + PAT + AHAS | | 2,4-D, Dichloprop, Fops, MCPA, MCPP (Mecoprop), Dims |
| | AAD-1 + GAT + ALS | | 2,4-D, Dichloprop, Fops, MCPA, MCPP (Mecoprop), Dims, ALS inhibitors not selective for in-corn application |
| | AAD-1 + PAT + GAT + ALS | | 2,4-D, Dichloprop, Fops, MCPA, MCPP (Mecoprop), Dims, ALS inhibitors not selective for in-corn application |
| GAT + ALS + PAT | AAD-1 | Fops, Dims, Paraquat, 2,4-D, Dichlorprop, MCPA, MCPP (Mecoprop), Dicamba, HPPD not recommended for corn | 2,4-D, Dichloprop, Fops, MCPA, MCPP (Mecoprop), Dims, |
| | AAD-1 + GT | | 2,4-D, Dichloprop, Fops, MCPA, MCPP (Mecoprop), Dims, |
| | AAD-1 + PAT | | 2,4-D, Dichloprop, Fops, MCPA, MCPP (Mecoprop), Dims, |
| | AAD-1 + AHAS | | 2,4-D, Dichloprop, Fops, MCPA, MCPP (Mecoprop), Dims, |

TABLE 2-continued

Control of volunteer corn (or other monocot) [trait alone or stacked with other HT traits] in AAD-1 Soybean or other dicot crops)

| Previous year Corn hybrid (or other monocot) | Current year Soybean variety (or other dicot) being planted | Herbicides option - Burndown/PRE | Herbicides option - POST |
|---|---|---|---|
| | AAD-1 + PAT + GT | | 2,4-D, Dichloprop, Fops, MCPA, MCPP (Mecoprop), Dims, |
| | AAD-1 + PAT + AHAS | | 2,4-D, Dichloprop, Fops, MCPA, MCPP (Mecoprop), Dims, |
| | AAD-1 + GAT + ALS | | 2,4-D, Dichloprop, Fops, MCPA, MCPP (Mecoprop), Dims, |
| | AAD-1 + PAT + GAT + ALS | | 2,4-D, Dichloprop, Fops, MCPA, MCPP (Mecoprop), Dims, |
| Dicamba | AAD-1 | Glufosinate, Glyphosate, Fops, Dims, IMI, Paraquat, 2,4-D, Dichlorprop, MCPA, MCPP (Mecoprop) other ALS herbicides not recommended for corn (need to be aware of planting restrictions) enabled by "ALS gene" | 2,4-D, Dichloprop, Fops, MCPA, MCPP (Mecoprop), Dims, IMI |
| | AAD-1 + GT | | 2,4-D, Dichloprop, Fops, MCPA, MCPP (Mecoprop), Dims, Glyphosate, IMI |
| | AAD-1 + PAT | | 2,4-D, Dichloprop, Fops, MCPA, MCPP (Mecoprop), Dims, Glufosinate, IMI |
| | AAD-1 + AHAS | | 2,4-D, Dichloprop, Fops, MCPA, MCPP (Mecoprop), Dims, IMI |
| | AAD-1 + PAT + GT | | 2,4-D, Dichloprop, Fops, MCPA, MCPP (Mecoprop), Dims, Glufosinate, Glyphosate, IMI |
| | AAD-1 + PAT + AHAS | | 2,4-D, Dichloprop, Fops, MCPA, MCPP (Mecoprop), Dims, Glufosinate, IMI |
| | AAD-1 + GAT + ALS | | 2,4-D, Dichloprop, Fops, MCPA, MCPP (Mecoprop), Dims, Glyphosate, IMI, ALS inhibitors not selective for in-corn application |
| | AAD-1 + PAT + GAT + ALS | | 2,4-D, Dichloprop, Fops, MCPA, MCPP (Mecoprop), Dims, Glufosinate, Glyphosate, IMI, ALS inhibitors not selective for in-corn application |
| HPPD | AAD-1 | Glufosinate, Glyphosate, Fops, Dims, IMI, Paraquat, 2,4-D, Dichlorprop, MCPA, MCPP (Mecoprop), Dicamba, HPPD not recommended for corn other ALS herbicides not recommended for corn (need to be aware of planting restrictions) enabled by "ALS gene" | 2,4-D, Dichloprop, Fops, MCPA, MCPP (Mecoprop), Dims, IMI |
| | AAD-1 + GT | | 2,4-D, Dichloprop, Fops, MCPA, MCPP (Mecoprop), Dims, Glyphosate, IMI |
| | AAD-1 + PAT | | 2,4-D, Dichloprop, Fops, MCPA, MCPP (Mecoprop), Dims, Glufosinate, IMI |
| | AAD-1 + AHAS | | 2,4-D, Dichloprop, Fops, MCPA, MCPP (Mecoprop), Dims, IMI |
| | AAD-1 + PAT + GT | | 2,4-D, Dichloprop, Fops, MCPA, MCPP (Mecoprop), Dims, Glufosinate, Glyphosate, IMI |
| | AAD-1 + PAT + AHAS | | 2,4-D, Dichloprop, Fops, MCPA, MCPP (Mecoprop), Dims, Glufosinate, IMI |
| | AAD-1 + GAT + ALS | | 2,4-D, Dichloprop, Fops, MCPA, MCPP (Mecoprop), Dims, Glyphosate, IMI, ALS inhibitors not selective for in-corn application |

TABLE 2-continued

Control of volunteer corn (or other monocot) [trait alone or stacked with other HT traits] in AAD-1 Soybean or other dicot crops)

| Previous year Corn hybrid (or other monocot) | Current year Soybean variety (or other dicot) being planted | Herbicides option - Burndown/PRE | Herbicides option - POST |
|---|---|---|---|
| | AAD-1 + PAT + GAT + ALS | | 2,4-D, Dichloprop, Fops, MCPA, MCPP (Mecoprop), Dims, Glufosinate, Glyphosate, IMI, ALS inhibitors not selective for in-corn application |

Gene and trait footnotes:

GT = any glyphosate specific tolerance trait including Roundup Ready (CP4), TIPS EPSPS (GA21, Glytol, DMMG), Athenix's EPSPS, GAT only without ALS, GOX, glyphosate decarboxylase, etc.

ALS = double mutant ALS gene insensitive to all ALS herbicide chemistries including IMI herbicides.

AAD-1 = Aryloxyalkanoate dioxygenase gene providing tolerance to all commercial phenoxy auxin and all aryloxyphenoxypropionate (fop) herbicides.

AAD-12 = Aryloxyalkanoate dioxygenase gene providing tolerance to phenoxyacetic auxin and pyridyloxyacetic auxin herbicides.

PAT = phosphinothricin acetyltransferase gene providing tolerance to glutamine synthetase inhibitors including, but not limited to, glufosinate. Similar phenotype is provided by genes such as BAR, DSM1, DSM2, et al.

AHAS = imidazolonine specific tolerance gene associated with point mutation at S623 of ALS gene (maize sequence) or equivalent amino acid in other spp (e.g., S653 in *Arabidopsis*).

RR = Roundup Ready trait, implies utility of CP4 gene as commercially deployed either alone or in combination with other genes but imparting glyphosate only tolerance.

CL = Clearfield crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.

LL = Liberty Link trait, implies utility of either PAT or BAR gene as commercially deployed either alone or in combination with other genes but imparting only tolerance to glutamine synthetase inhibitors such as glufosinate.

STS = designates resistance to sulfonylurea herbicide chemistry with use of ALS1 gene.

Herbicide footnotes:

IMI = any imidazolinone herbicide including, but not limited to, imazapyr, imazethapyr, imazamox, imazaquin.

DIMS = cyclohexanedione class of herbicides (dims) including, but not limited to, sethoxydim, clethodim, and for the purposes of this demonstration poinoxaden.

Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.

ALS inhibitors = any ALS inhibitor to the exclusion of IMI's for the sake of this demonstration (i.e., sulfonylureas, triazolopyrimidine sulfonanalides, sulfonylaminocarbonyltriazolinone).

HPPD = p-Hydroxyphenyl pyruvate dioxygenase inhibitor class of chemistry including but not limited to mesotrione, sulcotrione, isoxaflutole, and pyrazolynate.

MSMA and DSMA = herbicides from the organoarsenicals chemistry family.

N/A = No suitable options available postemergence.

TABLE 3

Control of volunteer corn (or other monocot) [trait alone or stacked with other HT traits] in AAD-12 Soybean (or other dicot crops)

| Previous year Corn hybrid (or other monocot) | Current year Soybean variety (or other dicot) being planted | Herbicides option - Burndown/PRE | Herbicides option - POST |
|---|---|---|---|
| | Appl: alone and tank mixes | | |
| Conventional corn | AAD-12 | Glufosinate, Glyphosate, Fops, Dims, IMI, Paraquat, 2,4-D, Dichlorprop, MCPA, MCPP (Mecoprop), Dicamba, HPPD not recommended for corn other ALS herbicides not recommended for corn (need to be aware of planting restrictions) enabled by "ALS gene" | 2,4-D, Dims, IMI |
| | AAD-12 + GT | | 2,4-D, Dims, Glyphosate, IMI |
| | AAD-12 + PAT | | 2,4-D, Dims, Glufosinate, IMI |
| | AAD-12 + AHAS | | 2,4-D, Dims, IMI |
| | AAD-12 + PAT + GT | | 2,4-D, Dims, Glufosinate, Glyphosate, IMI |
| | AAD-12 + PAT + AHAS | | 2,4-D, Dims, Glufosinate, IMI |
| | AAD-12 + GAT + ALS | | 2,4-D, Dims, Glyphosate, IMI, ALS inhibitors not selective for in-corn application |
| | AAD-12 + PAT + GAT + ALS | | 2,4-D, Dims, Glufosinate, Glyphosate, IMI, ALS inhibitors not selective for in-corn application |
| CL Corn | AAD-12 | Glufosinate, Glyphosate, Fops, Dims, Paraquat, 2,4-D, Dichlorprop, MCPA, MCPP (Mecoprop), Dicamba, HPPD not recommended for corn | 2,4-D, Dims |
| | AAD-12 + GT | | 2,4-D, Dims, Glyphosate, |
| | AAD-12 + PAT | | 2,4-D, Dims, Glufosinate, |
| | AAD-12 + AHAS | | 2,4-D, Dims, |
| | AAD-12 + PAT + GT | | 2,4-D, Dims, Glufosinate, Glyphosate, |

TABLE 3-continued

Control of volunteer corn (or other monocot) [trait alone or stacked with other HT traits] in AAD-12 Soybean (or other dicot crops)

| Previous year Corn hybrid (or other monocot) | Current year Soybean variety (or other dicot) being planted | Herbicides option - Burndown/PRE | Herbicides option - POST |
|---|---|---|---|
| | AAD-12 + PAT + AHAS | other ALS herbicides not recommended for corn (need to be aware of planting restrictions) enabled by "ALS gene" | 2,4-D, Dims, Glufosinate, |
| | AAD-12 + GAT + ALS | | 2,4-D, Dims, Glyphosate, ALS inhibitors not selective for in-corn application |
| | AAD-12 + PAT + GAT + ALS | | 2,4-D, Dims, Glufosinate, Glyphosate, ALS inhibitors not selective for in-corn application |
| RR or GT Corn | AAD-12 | Glufosinate, Fops, Dims, IMI, Paraquat, 2,4-D, Dichlorprop, MCPA, MCPP (Mecoprop), Dicamba, HPPD not recommended for corn | 2,4-D, Dims, IMI |
| | AAD-12 + GT | | 2,4-D, Dims, IMI |
| | AAD-12 + PAT | | 2,4-D, Dims, Glufosinate, IMI |
| | AAD-12 + AHAS | | 2,4-D, Dims, IMI |
| | AAD-12 + PAT + GT | | 2,4-D, Dims, Glufosinate, IMI |
| | AAD-12 + PAT + AHAS | | 2,4-D, Dims, Glufosinate, IMI |
| | AAD-12 + GAT + ALS | other ALS herbicides not recommended for corn (need to be aware of planting restrictions) enabled by "ALS gene" | 2,4-D, Dims, IMI, ALS inhibitors not selective for in-corn application |
| | AAD-12 + PAT + GAT + ALS | | 2,4-D, Dims, Glufosinate, IMI, ALS inhibitors not selective for in-corn application |
| LL Corn | AAD-12 | , Glyphosate, Fops, Dims, IMI, Paraquat, 2,4-D, Dichlorprop, MCPA, MCPP (Mecoprop), Dicamba, HPPD not recommended for corn | 2,4-D, Dims, IMI |
| | AAD-12 + GT | | 2,4-D, Dims, Glyphosate, IMI |
| | AAD-12 + PAT | | 2,4-D, Dims,, IMI |
| | AAD-12 + AHAS | | 2,4-D, Dims, IMI |
| | AAD-12 + PAT + GT | | 2,4-D, Dims,, Glyphosate, IMI |
| | AAD-12 + PAT + AHAS | | 2,4-D, Dims,, IMI |
| | AAD-12 + GAT + ALS | other ALS herbicides not recommended for corn (need to be aware of planting restrictions) enabled by "ALS gene" | 2,4-D, Dims, Glyphosate, IMI, ALS inhibitors not selective for in-corn application |
| | AAD-12 + PAT + GAT + ALS | | 2,4-D, Dims,, Glyphosate, IMI, ALS inhibitors not selective for in-corn application |
| GAT + ALS | AAD-12 | Glufosinate, Fops, Dims, Paraquat, 2,4-D, Dichlorprop, MCPA, MCPP (Mecoprop), Dicamba, HPPD not recommended for corn | 2,4-D, Dims |
| | AAD-12 + GT | | 2,4-D, Dims,, |
| | AAD-12 + PAT | | 2,4-D, Dims, Glufosinate |
| | AAD-12 + AHAS | | 2,4-D, Dims |
| | AAD-12 + PAT + GT | | 2,4-D, Dims, Glufosinate |
| | AAD-12 + PAT + AHAS | | 2,4-D, Dims, Glufosinate |
| | AAD-12 + GAT + ALS | | 2,4-D, Dims |
| | AAD-12 + PAT + FGAT + ALS | | 2,4-D, Dims, Glufosinate |
| CL (or AHAS) + PAT | AAD-12 | Glyphosate, Fops, Dims,, Paraquat, 2,4-D, Dichlorprop, MCPA, MCPP (Mecoprop), Dicamba, HPPD not recommended for corn | 2,4-D, Dims |
| | AAD-12 + GT | | 2,4-D, Dims, Glyphosate |
| | AAD-12 + PAT | | 2,4-D, Dims, |
| | AAD-12 + AHAS | | 2,4-D, Dims |
| | AAD-12 + PAT + GT | | 2,4-D, Dims, Glyphosate |
| | AAD-12 + PAT + AHAS | | 2,4-D, Dims |
| | AAD-12 + GAT + ALS | other ALS herbicides not recommended for corn (need to be aware of planting restrictions) enabled by "ALS gene" | 2,4-D, Dims, Glyphosate, ALS inhibitors not selective for in-corn application |
| | AAD-12 + PAT + GAT + ALS | | 2,4-D, Dims, Glyphosate, ALS inhibitors not selective for in-corn application |
| CL (or AHAS) + GT | AAD-12 | Glufosinate, Fops, Dims,, Paraquat, 2,4-D, Dichlorprop, MCPA, MCPP (Mecoprop), Dicamba, HPPD not recommended for corn | 2,4-D, Dims |
| | AAD-12 + GT | | 2,4-D, Dims, Glufosinate |
| | AAD-12 + PAT | | 2,4-D, Dims, |
| | AAD-12 + AHAS | | 2,4-D, Dims |
| | AAD-12 + PAT + GT | | 2,4-D, Dims, Glufosinate |
| | AAD-12 + PAT + AHAS | | 2,4-D, Dims |
| | AAD-12 + GAT + ALS | other ALS herbicides not recommended for corn (need to be aware of planting restrictions) enabled by "ALS gene" | 2,4-D, Dims, Glufosinate, ALS inhibitors not selective for in-corn application |
| | AAD-12 + PAT + GAT + ALS | | 2,4-D, Dims, Glufosinate, ALS inhibitors not selective for in-corn application |

TABLE 3-continued

Control of volunteer corn (or other monocot) [trait alone or stacked with other HT traits] in AAD-12 Soybean (or other dicot crops)

| Previous year Corn hybrid (or other monocot) | Current year Soybean variety (or other dicot) being planted | Herbicides option - Burndown/PRE | Herbicides option - POST |
|---|---|---|---|
| GT + PAT | AAD-12 | Fops, Dims, IMI, Paraquat, 2,4-D, Dichlorprop, MCPA, MCPP (Mecoprop), Dicamba, HPPD not recommended for corn other ALS herbicides not recommended for corn (need to be aware of planting restrictions) | 2,4-D, Dims, IMI |
| | AAD-12 + GT | | 2,4-D, Dims, IMI |
| | AAD-12 + PAT | | 2,4-D, Dims, IMI |
| | AAD-12 + AHAS | | 2,4-D, Dims, IMI |
| | AAD-12 + PAT + GT | | 2,4-D, Dims, IMI |
| | AAD-12 + PAT + AHAS | | 2,4-D, Dims, IMI |
| | AAD-12 + GAT + ALS | | 2,4-D, Dims, IMI, ALS inhibitors not selective for in-corn application |
| | AAD-12 + PAT + GAT + ALS | enabled by "ALS gene" | 2,4-D, Dims, IMI, ALS inhibitors not selective for in-corn application |
| GT + CL (or AHAS) + PAT | AAD-12 | Fops, Dims, Paraquat, 2,4-D, Dichlorprop, MCPA, MCPP (Mecoprop), Dicamba, HPPD not recommended for corn other ALS herbicides not recommended for corn (need to be aware of planting restrictions) | 2,4-D, Dims |
| | AAD-12 + GT | | 2,4-D, Dims |
| | AAD-12 + PAT | | 2,4-D, Dims |
| | AAD-12 + AHAS | | 2,4-D, Dims |
| | AAD-12 + PAT + GT | | 2,4-D, Dims |
| | AAD-12 + PAT + AHAS | | 2,4-D, Dims |
| | AAD-12 + GAT + ALS | | 2,4-D, Dims, ALS inhibitors not selective for in-corn application |
| | AAD-12 + PAT + GAT + ALS | enabled by "ALS gene" | 2,4-D, Dims, ALS inhibitors not selective for in-corn application |
| GAT + ALS + PAT | AAD-12 | Fops, Dims, Paraquat, 2,4-D, Dichlorprop, MCPA, MCPP (Mecoprop), Dicamba, HPPD not recommended for corn | 2,4-D, Dims, |
| | AAD-12 + GT | | 2,4-D, Dims, |
| | AAD-12 + PAT | | 2,4-D, Dims, |
| | AAD-12 + AHAS | | 2,4-D, Dims, |
| | AAD-12 + PAT + GT | | 2,4-D, Dims, |
| | AAD-12 + PAT + AHAS | | 2,4-D, Dims, |
| | AAD-12 + GAT + ALS | | 2,4-D, Dims, |
| | AAD-12 + PAT + GAT + ALS | | 2,4-D, Dims, |
| Dicamba | AAD-12 | Glufosinate, Glyphosate, Fops, Dims, IMI, Paraquat, 2,4-D, Dichlorprop, MCPA, MCPP (Mecoprop) other ALS herbicides not recommended for corn (need to be aware of planting restrictions) enabled by "ALS gene" | 2,4-D, Dims, IMI |
| | AAD-12 + GT | | 2,4-D, Dims, Glyphosate, IMI |
| | AAD-12 + PAT | | 2,4-D, Dims, Glufosinate, IMI |
| | AAD-12 + AHAS | | 2,4-D, Dims, IMI |
| | AAD-12 + PAT + GT | | 2,4-D, Dims, Glufosinate, Glyphosate, IMI |
| | AAD-12 + PAT + AHAS | | 2,4-D, Dims, Glufosinate, IMI |
| | AAD-12 + GAT + ALS | | 2,4-D, Dims, Glyphosate, IMI, ALS inhibitors not selective for in-corn application |
| | AAD-12 + PAT + GAT + ALS | | 2,4-D, Dims, Glufosinate, Glyphosate, IMI, ALS inhibitors not selective for in-corn application |
| HPPD | AAD-12 | Glufosinate, Glyphosate, Fops, Dims, IMI, Paraquat, 2,4-D, Dichlorprop, MCPA, MCPP (Mecoprop), Dicamba, HPPD not recommended for corn other ALS herbicides not recommended for corn (need to be aware of planting restrictions) | 2,4-D, Dims, IMI |
| | AAD-12 + GT | | 2,4-D, Dims, Glyphosate, IMI |
| | AAD-12 + PAT | | 2,4-D, Dims, Glufosinate, IMI |
| | AAD-12 + AHAS | | 2,4-D, Dims, IMI |
| | AAD-12 + PAT + GT | | 2,4-D, Dims, Glufosinate, Glyphosate, IMI |
| | AAD-12 + PAT + AHAS | | 2,4-D, Dims, Glufosinate, IMI |
| | AAD-12 + GAT + ALS | | 2,4-D, Dims, Glyphosate, IMI, ALS inhibitors not selective for in-corn application |

TABLE 3-continued

Control of volunteer corn (or other monocot) [trait alone or stacked with other HT traits] in AAD-12 Soybean (or other dicot crops)

| Previous year Corn hybrid (or other monocot) | Current year Soybean variety (or other dicot) being planted | Herbicides option - Burndown/PRE | Herbicides option - POST |
|---|---|---|---|
| | AAD-12 + PAT + GAT + ALS | enabled by "ALS gene" | 2,4-D, Dims, Glufosinate, Glyphosate, IMI, ALS inhibitors not selective for in-corn application |

Gene and trait footnotes:

GT = any glyphosate specific tolerance trait including Roundup Ready (CP4), TIPS EPSPS (GA21, Glytol, DMMG), Athenix's EPSPS, GAT only without ALS, GOX, glyphosate decarboxylase, etc.
ALS = double mutant ALS gene insensitive to all ALS herbicide chemistries including IMI herbicides.
AAD-1 = Aryloxyalkanoate dioxygenase gene providing tolerance to all commercial phenoxy auxin and all aryloxyphenoxypropionate (fop) herbicides.
AAD-12 = Aryloxyalkanoate dioxygenase gene providing tolerance to phenoxyacetic auxin and pyridyloxyacetic auxin herbicides.
PAT = phosphinothricin acetyltransferase gene providing tolerance to glutamine synthetase inhibitors including, but not limited to, glufosinate. Similar phenotype is provided by genes such as BAR, DSM1, DSM2, et al.
AHAS = imidazolonine specific tolerance gene associated with point mutation at S623 of ALS gene (maize sequence) or equivalent amino acid in other spp (e.g., S653 in *Arabidopsis*).
RR = Roundup Ready trait, implies utility of CP4 gene as commercially deployed either alone or in combination with other genes but imparting glyphosate only tolerance.
CL = Clearfield crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.
LL = Liberty Link trait, implies utility of either PAT or BAR gene as commercially deployed either alone or in combination with other genes but imparting only tolerance to glutamine synthetase inhibitors such as glufosinate.
STS = designates resistance to sulfonylurea herbicide chemistry with use of ALS1 gene.

Herbicide footnotes:

IMI = any imidazolinone herbicide including, but not limited to, imazapyr, imazethapyr, imazamox, imazaquin.
DIMS = cyclohexanedione class of herbicides (dims) including, but not limited to, sethoxydim, clethodim, and for the purposes of this demonstration poinoxaden.
Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.
ALS inhibitors = any ALS inhibitor to the exclusion of IMI's for the sake of this demonstration (i.e., sulfonylureas, triazolopyrimidine sulfonanalides, sulfonylaminocarbonyltriazolinone).
HPPD = p-Hydroxyphenyl pyruvate dioxygenase inhibitor class of chemistry including but not limited to mesotrione, sulcotrione, isoxaflutole, and pyrazolynate.
MSMA and DSMA = herbicides from the organoarsenicals chemistry family.
N/A = No suitable options available postemergence.

TABLE 4

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | | Appl: alone and tank mixes | | |
| AAD-1 | Cotton, CL Cotton, STS Cotton | Glyphosate, Dims, Tribenuron, Trifloxysulfuron, Paraquat, Glufosinate, MSMA, Flumioxazin, Pendimethalin, Trifluralin, Prometryn, Clomazone, | Prometryn, Lactofen, Fluometuron, DSMA, MSMA, Trifloxysulfuron, Oxyfluorfen, Paraquat, Dimethipin, Diuron, Linuron, Fomesafen, Flumioxazin, Dims, Imazapyr + Imazethapyr, imazamox, imazaquin | Pyrithiobac, Dims, Imazapyr + Imazethapyr, imazamox, imazaquin |
| | RR Cotton | Fluometuron, Diuron, Fomesafen, Pyrithiobac | Dims, Glyphosate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Glyphosate, Pyrithiobac |
| | LL Cotton | | Dims, Glufosinate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Glufosinate, Pyrithiobac |

TABLE 4-continued

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | GAT | | Dims, Glyphosate, ALS herbicides (imidazolinones, sulfonylureas, triazolopyrimidine sulfonanalides, sulfobylamino carbonyl triazolinones), Prometryn, Lactofen, Fluometuron, DSMA, MSMA, Oxyfluorfen, Paraquat, Dimethipin, Diuron, Linuron, Fomesafen, Flumioxazin | Dims, Glyphosate, ALS herbicides (imidazolinones, sulfonylureas, triazolopyrimidine sulfonanalides, sulfobylamino carbonyl triazolinones), Pyrithiobac |
| | AAD-12 | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |
| | AAD-12 + TIPS | | Dims, Glyphosate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Glyphosate, Pyrithiobac |
| | AAD-12 + PAT | | Dims, Glufosinate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Glufosinate, Pyrithiobac |
| | AAD-12 + AHAS | | Dims, Prometryn, Lactofen, Fluometuron, DSMA, MSMA, Sulfonylureas, Oxyfluorfen, Paraquat, Dimethipin, Diuron, Linuron, Fomesafen, Flumioxazin, | Dims, Pyrithiobac Sulfonylureas, |
| | AAD-12 + PAT + TIPS | | Dims, Glyphosate, glufosinate, Prometryn, Lactofen, Fluometuron, DSMA, MSMA, Trifloxysulfuron, Oxyfluorfen, Paraquat, Dimethipin, Diuron, Linuron, Fomesafen, Flumioxazin | Dims, Glyphosate, glufosinate, Pyrithiobac |
| | AAD-12 + PAT + AHAS | | Dims, glufosinate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, glufosinate, Sulfonylureas, Pyrithiobac |

TABLE 4-continued

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | AAD-12 + GAT | | Dims, Glyphosate, ALS herbicides (imidazolinones, sulfonylureas, triazolopyrimidine sulfonanalides, sulfobylamino carbonyl triazolinones), Prometryn, Lactofen, Fluometuron, DSMA, MSMA, Oxyfluorfen, Paraquat, Dimethipin, Diuron, Linuron, Fomesafen, Flumioxazin | Dims, Glyphosate, ALS herbicides (imidazolinones, sulfonylureas, triazolopyrimidine sulfonanalides, sulfobylamino carbonyl triazolinones), Pyrithiobac |
| AAD-1 + PAT | CL Cotton | Glyphosate, Dims, Tribenuron, Trifloxysulfuron, Paraquat, MSMA, Flumioxazin, Pendimethalin, Trifluralin, Prometryn, Clomazone, Fluometuron, Diuron, Fomesafen, | Dims, Imazapyr + Imazethapyr, imazamox, imazaquin, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Pyrithiobac, Dims, Imazapyr + Imazethapyr, imazamox, imazaquin |
| | RR Cotton | Pyrithiobac | Dims, Glyphosate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Glyphosate, Pyrithiobac |
| | LL Cotton | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin | Dims,, Pyrithiobac |
| | GAT | | Dims, Glyphosate, ALS herbicides (imidazolinones, sulfonylureas, triazolopyrimidine sulfonanalides, sulfobylamino carbonyl triazolinones) | Dims, Glyphosate, ALS herbicides (imidazolinones, sulfonylureas, triazolopyrimidine sulfonanalides, sulfobylamino carbonyl triazolinones), Pyrithiobac |
| | AAD-12 | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |
| | AAD-12 + TIPS | | Glyphosate, Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin | Dims, Glyphosate, Pyrithiobac |
| | AAD-12 + PAT | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin | Dims,, Pyrithiobac |

TABLE 4-continued

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | AAD-12 + AHAS | | Dims, Prometryn, Lactofen, Fluometuron, DSMA, MSMA, Sulfonylureas, Oxyfluorfen, Paraquat, Dimethipin, Diuron, Linuron, Fomesafen, Flumioxazin | Dims, Pyrithiobac Sulfonylureas, |
| | AAD-12 + PAT + TIPS | | Dims, Glyphosate, Prometryn, Lactofen, Fluometuron, DSMA, MSMA, Trifloxysulfuron, Oxyfluorfen, Paraquat, Dimethipin, Diuron, Linuron, Fomesafen, Flumioxazin | Dims, Glyphosate,, Pyrithiobac |
| | AAD-12 + PAT + AHAS | | Dims, Prometryn, Lactofen, Fluometuron, DSMA, MSMA, Sulfonylureas, Oxyfluorfen, Paraquat, Dimethipin, Diuron, Linuron, Fomesafen, Flumioxazin | Dims,, Sulfonylureas, Pyrithiobac |
| | AAD-12 + GAT | | Dims, Glyphosate, ALS herbicides (imidazolinones, sulfonylureas, triazolopyrimidine sulfonanalides, sulfobylamino carbonyl triazolinones), Prometryn, Lactofen, Fluometuron, DSMA, MSMA, Oxyfluorfen, Paraquat, Dimethipin, Diuron, Linuron, Fomesafen, Flumioxazin | Dims, Glyphosate, ALS herbicides (imidazolinones, sulfonylureas, triazolopyrimidine sulfonanalides, sulfobylamino carbonyl triazolinones), Pyrithiobac |
| AAD-1 + TIPS | CL Cotton | Dims, Tribenuron, Trifloxysulfuron, Paraquat, Glufosinate, MSMA, Flumioxazin, Pendimethalin, Trifluralin, Prometryn, Clomazone, Fluometuron, Diuron, Fomesafen, Pyrithiobac | Prometryn, Lactofen, Fluometuron, DSMA, MSMA, Trifloxysulfuron, Oxyfluorfen, Paraquat, Dimethipin, Diuron, Linuron, Fomesafen, Flumioxazin, Dims, Imazapyr + Imazethapyr, imazamox, imazaquin | Pyrithiobac, Dims, Imazapyr + Imazethapyr, imazamox, imazaquin |
| | RR Cotton | Fomesafen, Pyrithiobac | Dims, Glyphosate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |
| | LL Cotton | | Dims, Glufosinate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Glufosinate, Pyrithiobac |

TABLE 4-continued

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | GAT | | Dims, ALS herbicides (imidazolinones, sulfonylureas, triazolopyrimidine sulfonanalides, sulfobylamino carbonyl triazolinones), Prometryn, Lactofen, Fluometuron, DSMA, MSMA, Oxyfluorfen, Paraquat, Dimethipin, Diuron, Linuron, Fomesafen, Flumioxazin | Dims, ALS herbicides (imidazolinones, sulfonylureas, triazolopyrimidine sulfonanalides, sulfobylamino carbonyl triazolinones), Pyrithiobac |
| | AAD-12 | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |
| | AAD-12 + TIPS | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |
| | AAD-12 + PAT | | Dims, Glufosinate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Glufosinate, Pyrithiobac |
| | AAD-12 + AHAS | | Dims, Prometryn, Lactofen, Fluometuron, DSMA, MSMA, Sulfonylureas, Oxyfluorfen, Paraquat, Dimethipin, Diuron, Linuron, Fomesafen, Flumioxazin, | Dims, Pyrithiobac Sulfonylureas, |
| | AAD-12 + PAT + TIPS | | Dims, glufosinate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, glufosinate, Pyrithiobac |
| | AAD-12 + PAT + AHAS | | Dims, Glufosinate, Prometryn, Lactofen, Fluometuron, DSMA, MSMA, Sulfonylureas, Oxyfluorfen, Paraquat, Dimethipin, Diuron, Linuron, Fomesafen, Flumioxazin, | Dims, glufosinate, Sulfonylureas, Pyrithiobac |
| | AAD-12 + GAT | | Dims, ALS herbicides (imidazolinones, sulfonylureas, triazolopyrimidine sulfonanalides, sulfobylamino carbonyl triazolinones), Prometryn, Lactofen, Fluometuron, DSMA, MSMA, Oxyfluorfen, Paraquat, Dimethipin, Diuron, Linuron, Fomesafen, Flumioxazin | Dims, ALS herbicides (imidazolinones, sulfonylureas, triazolopyrimidine sulfonanalides, sulfobylamino carbonyl triazolinones), Pyrithiobac |

TABLE 4-continued

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| AAD-1 + AHAS | CL Cotton | Glyphosate, Dims, Tribenuron, Trifloxysulfuron, Paraquat, Glufosinate, MSMA, Flumioxazin, Pendimethalin, Trifluralin, Prometryn, Clomazone, Fluometuron, Diuron, Fomesafen, Pyrithiobac | Dims, Imazapyr + Imazethapyr, imazamox, imazaquin, Prometryn, Lactofen, Fluometuron, DSMA, MSMA, Oxyfluorfen, Paraquat, Dimethipin, Diuron, Linuron, Fomesafen, Flumioxazin, | Pyrithiobac, Dims, Imazapyr + Imazethapyr, imazamox, imazaquin |
|  | RR Cotton |  | Dims, Glyphosate, Prometryn, Lactofen, Fluometuron, DSMA, MSMA, Oxyfluorfen, Paraquat, Dimethipin, Diuron, Linuron, Fomesafen, Flumioxazin, | Dims, Glyphosate, Pyrithiobac |
|  | LL Cotton |  | Dims, Prometryn, Lactofen, Fluometuron, Glufosinate, DSMA, MSMA, Oxyfluorfen, Paraquat Dimethipin, Diuron, Linuron, Fomesafen, Flumioxazin | Dims, Glufosinate, Pyrithiobac |
|  | GAT |  | Dims, ALS herbicides (imidazolinones, triazolopyrimidine sulfonanalides, sulfobylamino carbonyl triazolinones), Prometryn, Lactofen, Fluometuron, Glufosinate, DSMA, MSMA, Oxyfluorfen, Paraquat, Dimethipin, Diuron, Linuron, Fomesafen, Flumioxazin | Dims, Glyphosate, ALS herbicides (imidazolinones, triazolopyrimidine sulfonanalides, sulfobylamino carbonyl triazolinones), Pyrithiobac |
|  | AAD-12 |  | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
|  | AAD-12 + TIPS |  | Glyphosate, Dims, Prometryn, Lactofen, Fluometuron, DSMA, MSMA, Oxyfluorfen, Paraquat, Dimethipin, Diuron, Linuron, Fomesafen, Flumioxazin | Dims, Glyphosate, Pyrithiobac |
|  | AAD-12 + PAT |  | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin | Dims, Glufosinate, Pyrithiobac |
|  | AAD-12 + AHAS |  | Dims, Prometryn, Lactofen, Fluometuron, DSMA, MSMA, Oxyfluorfen, Paraquat, Dimethipin, Diuron, Linuron, Fomesafen, Flumioxazin | Dims, Pyrithiobac |

TABLE 4-continued

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | AAD-12 + PAT + TIPS | | Dims, Glyphosate, Prometryn, Lactofen, Fluometuron, DSMA, MSMA, Trifloxysulfuron, Oxyfluorfen, Paraquat, Dimethipin, Diuron, Linuron, Fomesafen, Flumioxazin | Dims, Glyphosate, glufosinate, Pyrithiobac |
| | AAD-12 + PAT + AHAS | | Dims, Glufosinate, Prometryn, Lactofen, Fluometuron, DSMA, MSMA, Oxyfluorfen, Paraquat, Dimethipin, Diuron, Linuron, Fomesafen, Flumioxazin | Dims, glufosinate, Pyrithiobac |
| | AAD-12 + GAT | | Dims, Glyphosate, ALS herbicides (imidazolinones, triazolopyrimidine sulfonanalides, sulfobylamino carbonyl triazolinones), Prometryn, Lactofen, Fluometuron, DSMA, MSMA, Oxyfluorfen, Paraquat, Dimethipin, Diuron, Linuron, Fomesafen, Flumioxazin | Dims, Glyphosate, ALS herbicides (imidazolinones, triazolopyrimidine sulfonanalides, sulfobylamino carbonyl triazolinones), Pyrithiobac |
| AAD-1 + PAT + TIPS | CL Cotton | Dims, Tribenuron, Trifloxysulfuron, Paraquat, MSMA, Flumioxazin, Pendimethalin, Trifluralin, Prometryn, Clomazone, Fluometuron, Diuron, Fomesafen, | Prometryn, Lactofen, Fluometuron, DSMA, MSMA, Trifloxysulfuron, Oxyfluorfen, Paraquat, Dimethipin, Diuron, Linuron, Fomesafen, Flumioxazin, Dims, Imazapyr + Imazethapyr, imazamox, imazaquin | Pyrithiobac, Dims, Imazapyr + Imazethapyr, imazamox, imazaquin |
| | RR Cotton | Pyrithiobac | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |
| | LL Cotton | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |
| | GAT | | Dims, ALS herbicides (imidazolinones, sulfonylureas, triazolopyrimidine sulfonanalides, sulfobylamino carbonyl triazolinones), Prometryn, Lactofen, Fluometuron, DSMA, MSMA, Oxyfluorfen, Paraquat, Dimethipin, Diuron, Linuron, Fomesafen, Flumioxazin | Dims, ALS herbicides (imidazolinones, sulfonylureas, triazolopyrimidine sulfonanalides, sulfobylamino carbonyl triazolinones), Pyrithiobac |
| | AAD-12 | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |

TABLE 4-continued

Control of volunteer AAD-1 corn (or other monocot crop) (alone or
stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | AAD-12 + TIPS | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |
| | AAD-12 + PAT | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |
| | AAD-12 + AHAS | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac Sulfonylureas, |
| | AAD-12 + PAT + TIPS | | Dims, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Pyrithiobac |
| | AAD-12 + PAT + AHAS | | Dims, Prometryn, Lactofen, Fluometuron, DSMA, MSMA, Sulfonylureas, Oxyfluorfen, Paraquat, Dimethipin, Diuron, Linuron, Fomesafen, Flumioxazin, | Dims, Sulfonylureas, Pyrithiobac |
| | AAD-12 + GAT | | Dims, ALS herbicides (imidazolinones, sulfonylureas, triazolopyrimidine sulfonanalides, sulfobylamino carbonyl triazolinones), Prometryn, Lactofen, Fluometuron, DSMA, MSMA, Oxyfluorfen, Paraquat, Dimethipin, Diuron, Linuron, Fomesafen, Flumioxazin | Dims, ALS herbicides (imidazolinones, sulfonylureas, triazolopyrimidine sulfonanalides, sulfobylamino carbonyl triazolinones), Pyrithiobac |
| AAD-1 + PAT + AHAS | CL Cotton | Glyphosate, Dims, Tribenuron, Trifloxysulfuron, Paraquat, MSMA, Flumioxazin, Pendimethalin, Trifluralin, Prometryn, Clomazone, Fluometuron, Diuron, Fomesafen, Pyrithiobac | Prometryn, Lactofen, Fluometuron, DSMA, MSMA, Oxyfluorfen, Paraquat, Dimethipin, Diuron, Linuron, Fomesafen, Flumioxazin, Dims, Imazapyr + Imazethapyr, imazamox, imazaquin | Pyrithiobac, Dims, Imazapyr + Imazethapyr, imazamox, imazaquin |
| | RR Cotton | | Dims, Glyphosate, Prometryn, Lactofen, Fluometuron, DSMA, MSMA, Oxyfluorfen, Paraquat, Dimethipin, Diuron, Linuron, Fomesafen, Flumioxazin, | Dims, Glyphosate, Pyrithiobac |

TABLE 4-continued

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | LL Cotton | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | GAT | | Dims, ALS herbicides (imidazolinones, triazolopyrimidine sulfonanalides, sulfobylamino carbonyl triazolinones), Prometryn, Lactofen, Fluometuron, DSMA, MSMA, Oxyfluorfen, Paraquat, Dimethipin, Diuron, Linuron, Fomesafen, Flumioxazin | Dims, Glyphosate, ALS herbicides (imidazolinones, triazolopyrimidine sulfonanalides, sulfobylamino carbonyl triazolinones), Pyrithiobac |
| | AAD-12 | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | AAD-12 + TIPS | | Dims, Glyphosate, Prometryn, Lactofen, Fluometuron, DSMA, MSMA, Oxyfluorfen, Paraquat, Dimethipin, Diuron, Linuron, Fomesafen, Flumioxazin, | Dims, Glyphosate, Pyrithiobac |
| | AAD-12 + PAT | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | AAD-12 + AHAS | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | AAD-12 + PAT + TIPS | | Dims, Glyphosate, Prometryn, Lactofen, Fluometuron, DSMA, MSMA, Trifloxysulfuron, Oxyfluorfen, Paraquat, Dimethipin, Diuron, Linuron, Fomesafen, Flumioxazin, | Dims, Glyphosate, Pyrithiobac |
| | AAD-12 + PAT + AHAS | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |

TABLE 4-continued

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | AAD-12 + GAT | | Dims, ALS herbicides (imidazolinones, triazolopyrimidine sulfonanalides, sulfobylamino carbonyl triazolinones), Prometryn, Lactofen, Fluometuron, DSMA, MSMA, Oxyfluorfen, Paraquat, Dimethipin, Diuron, Linuron, Fomesafen, Flumioxazin | Dims, Glyphosate, ALS herbicides (imidazolinones, triazolopyrimidine sulfonanalides, sulfobylamino carbonyl triazolinones), Pyrithiobac |
| AAD-1 + GAT | CL Cotton | Dims, Tribenuron, Trifloxysulfuron, Paraquat, Glufosinate, MSMA, Flumioxazin, Pendimethalin, Trifluralin, Prometryn, Clomazone, Fluometuron, Diuron, Fomesafen, Pyrithiobac | Prometryn, Lactofen, Fluometuron, DSMA, MSMA, Oxyfluorfen, Paraquat, Dimethipin, Diuron, Linuron, Fomesafen, Flumioxazin, Dims, | Pyrithiobac, Dims, Imazapyr + Imazethapyr, imazamox, imazaquin |
| | RR Cotton | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | LL Cotton | | Dims, Glufosinate, Prometryn, Lactofen, Fluometuron, DSMA, MSMA, Oxyfluorfen, Paraquat, Dimethipin, Diuron, Linuron, Fomesafen, Flumioxazin, | Dims, Glufosinate, Pyrithiobac |
| | GAT | | Dims, Prometryn, Lactofen, Fluometuron, DSMA, MSMA, Oxyfluorfen, Paraquat, Dimethipin, Diuron, Linuron, Fomesafen, Flumioxazin | Dims, Pyrithiobac |
| | AAD-12 | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | AAD-12 + TIPS | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | AAD-12 + PAT | | Dims, Glufosinate, Prometryn, Lactofen, Fluometuron, DSMA, MSMA, Oxyfluorfen, Paraquat, Dimethipin, Diuron, Linuron, Fomesafen, Flumioxazin, | Dims, Glufosinate, Pyrithiobac |
| | AAD-12 + AHAS | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |

TABLE 4-continued

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | AAD-12 + PAT + TIPS | | Dims, Prometryn, Lactofen, Fluometuron, DSMA, MSMA, Oxyfluorfen, Paraquat, Dimethipin, Diuron, Linuron, Fomesafen, Flumioxazin, | Dims, glufosinate, Pyrithiobac |
| | AAD-12 + PAT + AHAS | | Dims, Prometryn, Lactofen, Fluometuron, DSMA, MSMA, Oxyfluorfen, Paraquat, Dimethipin, Diuron, Linuron, Fomesafen, Flumioxazin, | Dims, glufosinate, Pyrithiobac |
| | AAD-12 + GAT | | Dims, Prometryn, Lactofen, Fluometuron, DSMA, MSMA, Oxyfluorfen, Paraquat, Dimethipin, Diuron, Linuron, Fomesafen, Flumioxazin | Dims, Pyrithiobac |
| AAD-1 + PAT + GAT | CL Cotton | Dims, Tribenuron, Trifloxysulfuron, Paraquat, Glufosinate, MSMA, Flumioxazin, Pendimethalin, Trifluralin, Prometryn, Dims, | Prometryn, Lactofen, Fluometuron, DSMA, MSMA, Oxyfluorfen, Paraquat, Dimethipin, Diuron, Linuron, Fomesafen, Flumioxazin, | Pyrithiobac, Dims, Imazapyr + Imazethapyr, imazamox, imazaquin |
| | RR Cotton | Clomazone, Fluometuron, Diuron, Fomesafen, Pyrithiobac | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | LL Cotton | | Dims, Glufosinate, Prometryn, Lactofen, Fluometuron, DSMA, MSMA, Oxyfluorfen, Paraquat, Dimethipin, Diuron, Linuron, Fomesafen, Flumioxazin, | Dims, Glufosinate, Pyrithiobac |
| | GAT | | Dims, Prometryn, Lactofen, Fluometuron, DSMA, MSMA, Oxyfluorfen, Paraquat, Dimethipin, Diuron, Linuron, Fomesafen, Flumioxazin | Dims, Pyrithiobac |
| | AAD-12 | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | AAD-12 + TIPS | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | AAD-12 + PAT | | Dims, Glufosinate, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |

TABLE 4-continued

Control of volunteer AAD-1 corn (or other monocot crop) (alone or stacked with other HT traits) in AAD-12-based Cotton (or other dicot crop)

| Previous year Corn hybrid | Current year Cotton hybrid being planted | Herbicides option - Burndown/PRE/PPI | Herbicides option - POST DIRECTED | Herbicides option - POST BROADCAST |
|---|---|---|---|---|
| | AAD-12 + AHAS | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | AAD-12 + PAT + TIPS | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | AAD-12 + PAT + AHAS | | Dims, Prometryn, Lactofen, Fluometuron, DSMA, MSMA, Oxyfluorfen, Paraquat, Dimethipin, Diuron, Linuron, Fomesafen, Flumioxazin, | Dims, Pyrithiobac |
| | AAD-12 + GAT | | Dims, Prometryn, Lactofen, Fluometuron, DSMA, MSMA, Oxyfluorfen, Paraquat, Dimethipin, Diuron, Linuron, Fomesafen, Flumioxazin | Dims, Pyrithiobac |

Gene and trait footnotes:
GT = any glyphosate specific tolerance trait including Roundup Ready (CP4), TIPS EPSPS (GA21, Glytol, DMMG), Athenix's EPSPS, GAT only without ALS, GOX, glyphosate decarboxylase, etc.
ALS = double mutant ALS gene insensitive to all ALS herbicide chemistries including IMI herbicides.
AAD-1 = Aryloxyalkanoate dioxygenase gene providing tolerance to all commercial phenoxy auxin and all aryloxyphenoxypropionate (fop) herbicides.
AAD-12 = Aryloxyalkanoate dioxygenase gene providing tolerance to phenoxyacetic auxin and pyridyloxyacetic auxin herbicides.
PAT = phosphinothricin acetyltransferase gene providing tolerance to glutamine synthetase inhibitors including, but not limited to, glufosinate. Similar phenotype is provided by genes such as BAR, DSM1, DSM2, et al.
AHAS = imidazolinone specific tolerance gene associated with point mutation at S623 of ALS gene (maize sequence) or equivalent amino acid in other spp (e.g., S653 in *Arabidopsis*).
RR = Roundup Ready trait, implies utility of CP4 gene as commercially deployed either alone or in combination with other genes but imparting glyphosate only tolerance.
CL = Clearfield crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.
LL = Liberty Link trait, implies utility of either PAT or BAR gene as commercially deployed either alone or in combination with other genes but imparting only tolerance to glutamine synthetase inhibitors such as glufosinate.
STS = designates resistance to sulfonylurea herbicide chemistry with use of ALS1 gene.
Herbicide footnotes:
IMI = any imidazolinone herbicide including, but not limited to, imazapyr, imazethapyr, imazamox, imazaquin.
DIMS = cyclohexanedione class of herbicides (dims) including, but not limited to, sethoxydim, clethodim, and for the purposes of this demonstration poinoxaden.
Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.
ALS inhibitors = any ALS inhibitor to the exclusion of IMI's for the sake of this demonstration (i.e., sulfonylureas, triazolopyrimidine sulfonanalides, sulfonylaminocarbonyltriazolinone).
HPPD = p-Hydroxyphenyl pyruvate dioxygenase inhibitor class of chemistry including but not limited to mesotrione, sulcotrione, isoxaflutole, and pyrazolynate.
MSMA and DSMA = herbicides from the organoarsenicals chemistry family.
N/A = No suitable options available postemergence.

Example 4

Control of Volunteer AAD Maize in a Field Planted with Maize Using Alternative Herbicides In another embodiment, volunteer transgenic maize lines containing the AAD expression cassette (AAD-1) are controlled within a field of maize by the application of a herbicide or combination of herbicides. The specific herbicide used to control the volunteer transgenic AAD maize line is dependent upon the type of maize seed being planted within the field (e.g., Clear Field Maize, Round-up Ready Maize, Liberty Link Maize, etc.).

Furthermore, the AAD trait may be stacked with other additional herbicide tolerant trait(s) via conventional breeding or a molecular stack. In such an example, the specific herbicide used to control the volunteer AAD maize stacked with another herbicide tolerant trait(s) will be dependent upon the additional herbicide tolerant trait(s) and the type of maize being planted within the field.

The application of a given herbicide can be made before planting at pre-emergence/burndown or post-emergence after planting to control the volunteer transgenic AAD maize lines. Table 5 lists the herbicides to be used at the different stages of planting (pre-emergence or post-emergence) to control volunteer transgenic AAD maize. At or about a 1× Field Rate concentration of herbicide would be applied, as either a tank mix or alone, to the field for both pre-emergent and post-emergent volunteer control.

The control of transgenic maize plants containing the AAD expression cassette within a field of maize would be applicable for the control of an AAD transgenic monocot plant (including, but not limited too; corn, rice, sugar cane, switch grass, turf grass species, sorghum, barley, wheat, and oats, and durum) within a field being planted with a monocot crop (including, but not limited too; corn, rice, sugar cane, switch grass, turf grass species, sorghum, barley, wheat, and oats, and durum). The example described above, in which volunteer transgenic AAD maize plants are controlled in a maize field, is illustrative of the invention and not intended to restrict the scope of this embodiment.

TABLE 5

Control of volunteer AAD-1 (trait alone or stacked with other HT traits) corn (or other monocot) in corn (or other monocot)

| Previous year Corn hybrid | 2008 Corn hybrid being planted | Herbicides option - Burndown/PRE | Herbicides option - POST |
|---|---|---|---|
| | Application: alone and tank mixes | | |
| AAD-1 | CL Corn | Glyphosate, Dims, glufosinate, paraquat | IMI |
| | RR Corn | | glyphosate |
| | LL Corn | IMI or other ALS herbicides not recommended for corn (need to be aware of planting restrictions) | glufosinate |
| | GAT + ALS | | glyphosate, IMI, ALS inhibitors not usually recommended for in-corn application |
| | AAD-1 + PAT | | glufosinate |
| | AAD-1 + GT | | glyphosate |
| | AAD-1 + AHAS | | IMI |
| | AAD-1 + PAT + GT | | glufosinate, glyphosate |
| | AAD-1 + PAT + AHAS | | glufosinate, glyphosate, IMI |
| | AAD-1 + PAT + GAT | | Glyphosate, glufosinate, IMI, ALS inhibitors not usually recommended for in-corn application |
| | AAD-1 + GAT | | glyphosate, ALS inhibitors not usually recommended for in-corn application |
| AAD-1 + PAT | CL Corn | Glyphosate, Dims, paraquat | IMI |
| | RR Corn | | glyphosate |
| | LL Corn | IMI or other ALS herbicides not recommended for corn (need to be aware of planting restrictions) | N/A |
| | GAT | | glyphosate, Imazapyr + imazethapyr, imazamox, imazaquin, ALS inhibitors not usually recommended for in-corn application |
| | AAD-1 Corn | | N/A |
| | AAD-1 + GT | | glyphosate |
| | AAD-1 + AHAS | | IMI |
| | AAD-1 + PAT + GT | | glyphosate |
| | AAD-1 + PAT + AHAS | | IMI |
| | AAD-1 + PAT + GAT | | glufosinate, IMI, ALS inhibitors not usually recommended for in-corn application |
| | AAD-1 + GAT | | glyphosate, IMI, ALS inhibitors not usually recommended for in-corn application |
| AAD-1 + GT | CL Corn | Dims, glufosinate, paraquat | IMI |
| | RR Corn | | N/A |
| | LL Corn | IMI or other ALS herbicides not recommended for corn (need to be aware of planting restrictions) | glufosinate |
| | GAT | | IMI, ALS inhibitors not usually recommended for in-corn application |
| | AAD-1 Corn | | N/A |
| | AAD-1 + PAT | | glufosinate |
| | AAD-1 + AHAS | | IMI |
| | AAD-1 + PAT + GT | | glufosinate |
| | AAD-1 + PAT + AHAS | | Glufosinate, IMI |
| | AAD-1 + GAT | | IMI, ALS inhibitors not usually recommended for in-corn application |
| | AAD-1 + PAT + GAT | | glufosinate, IMI, ALS inhibitors not usually recommended for in-corn application |

TABLE 5-continued

Control of volunteer AAD-1 (trait alone or stacked with other HT traits) corn (or other monocot) in corn (or other monocot)

| Previous year Corn hybrid | 2008 Corn hybrid being planted | Herbicides option - Burndown/PRE | Herbicides option - POST |
|---|---|---|---|
| AAD-1 + AHAS | CL Corn | Glyphosate, Dims, glufosinate, paraquat ALS herbicides not recommended for corn (need to be aware of planting restrictions) | N/A |
|  | RR Corn |  | glyphosate |
|  | LL Corn |  | glufosinate |
|  | GAT |  | IMI, ALS inhibitors not usually recommended for in-corn application |
|  | AAD-1 Corn |  | N/A |
|  | AAD-1 + PAT |  | glufosinate |
|  | AAD-1 + GT |  | glyphosate |
|  | AAD-1 + PAT + GT |  | glufosinate, glyphosate |
|  | AAD-1 + PAT + AHAS |  | glufosinate |
|  | AAD-1 + GAT |  | Glyphosate, ALS inhibitors not usually recommended for in-corn application |
|  | AAD-1 + PAT + GAT |  | Glyphosate, glufosinate, ALS inhibitors not usually recommended for in-corn application |
| AAD-1 + PAT + GT | CL Corn | Dims, paraquat IMI or other ALS herbicides not recommended for corn (need to be aware of planting restrictions) | IMI |
|  | RR Corn |  | N/A |
|  | LL Corn |  | N/A |
|  | GAT |  | IMI, ALS inhibitors not usually recommended for in-corn application |
|  | AAD-1 |  | N/A |
|  | AAD-1 + PAT |  | N/A |
|  | AAD-1 + GT |  | N/A |
|  | AAD-1 + AHAS |  | IMI |
|  | AAD-1 + PAT + AHAS |  | IMI |
|  | AAD-1 + GAT |  | ALS inhibitors not usually recommended for in-corn application |
|  | AAD-1 + PAT + GAT |  | ALS inhibitors not usually recommended for in-corn application |
| AAD-1 + PAT + AHAS | CL Corn | Glyphosate, Dims, paraquat IMI or other ALS herbicides not recommended for corn (need to be aware of planting restrictions) | N/A |
|  | RR Corn |  | glyphosate |
|  | LL Corn |  | N/A |
|  | GAT |  | Glyphosate, ALS inhibitors not usually recommended for in-corn application |
|  | AAD-1 |  | N/A |
|  | AAD-1 + PAT |  | N/A |
|  | AAD-1 + GT |  | glyphosate |
|  | AAD-1 + AHAS |  | N/A |
|  | AAD-1 + PAT + GT |  | glyphosate |
|  | AAD-1 + GAT |  | glyphosate, ALS inhibitors not usually recommended for in-corn application |
|  | AAD-1 + PAT + GAT + ALS |  | glyphosate, ALS inhibitors not usually recommended for in-corn application |
| AAD-1 + GAT + ALS | CL Corn | Dims, glufosinate, paraquat IMI or other ALS herbicides not recommended for corn (need to be aware of planting restrictions) | N/A |
|  | RR Corn |  | N/A |
|  | LL Corn |  | glufosinate |
|  | GAT + ALS |  | N/A |
|  | AAD-1 |  | N/A |
|  | AAD-1 + PAT |  | glufosinate |
|  | AAD-1 + GT |  | N/A |
|  | AAD-1 + AHAS |  | N/A |
|  | AAD-1 + PAT + GT |  | glufosinate |
|  | AAD-1 + PAT + AHAS |  | glufosinate |
|  | AAD-1 + PAT + GAT + ALS |  | glufosinate |

TABLE 5-continued

Control of volunteer AAD-1 (trait alone or stacked with other HT traits)
corn (or other monocot) in corn (or other monocot)

| Previous year Corn hybrid | 2008 Corn hybrid being planted | Herbicides option - Burndown/PRE | Herbicides option - POST |
|---|---|---|---|
| AAD-1 + PAT + GAT + ALS | CL Corn | Dims, paraquat | N/A |
| | RR Corn | IMI or other ALS | N/A |
| | LL Corn | herbicides not | N/A |
| | GAT + ALS | recommended for corn | N/A |
| | AAD-1 | (need to be aware of | N/A |
| | AAD-1 + PAT | planting restrictions) | N/A |
| | AAD-1 + GT | | N/A |
| | AAD-1 + AHAS | | N/A |
| | AAD-1 + PAT + GT | | N/A |
| | AAD-1 + PAT + AHAS | | N/A |

Gene and trait footnotes:
GT = any glyphosate specific tolerance trait including Roundup Ready (CP4), TIPS EPSPS (GA21, Glytol, DMMG), Athenix's EPSPS, GAT only without ALS, GOX, glyphosate decarboxylase, etc.
ALS = double mutant ALS gene insensitive to all ALS herbicide chemistries including IMI herbicides.
AAD-1 = Aryloxyalkanoate dioxygenase gene providing tolerance to all commercial phenoxy auxin and all aryloxyphenoxypropionate (fop) herbicides.
AAD-12 = Aryloxyalkanoate dioxygenase gene providing tolerance to phenoxyacetic auxin and pyridyloxyacetic auxin herbicides.
PAT = phosphinothricin acetyltransferase gene providing tolerance to glutamine synthetase inhibitors including, but not limited to, glufosinate. Similar phenotype is provided by genes such as BAR, DSM1, DSM2, et al.
AHAS = imidazolonine specific tolerance gene associated with point mutation at S623 of ALS gene (maize sequence) or equivalent amino acid in other spp (e.g., S653 in *Arabidopsis*).
RR = Roundup Ready trait, implies utility of CP4 gene as commercially deployed either alone or in combination with other genes but imparting glyphosate only tolerance.
CL = Clearfield crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.
LL = Liberty Link trait, implies utility of either PAT or BAR gene as commercially deployed either alone or in combination with other genes but imparting only tolerance to glutamine synthetase inhibitors such as glufosinate.
STS = designates resistance to sulfonylurea herbicide chemistry with use of ALS1 gene.
Herbicide footnotes:
IMI = any imidazolinone herbicide including, but not limited to, imazapyr, imazethapyr, imazamox, imazaquin.
DIMS = cyclohexanedione class of herbicides (dims) including, but not limited to, sethoxydim, clethodim, and for the purposes of this demonstration poinoxaden.
Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.
ALS inhibitors = any ALS inhibitor to the exclusion of IMI's for the sake of this demonstration (i.e., sulfonylureas, triazolopyrimidine sulfonanalides, sulfonylaminocarbonyltriazolinone).
HPPD = p-Hydroxyphenyl pyruvate dioxygenase inhibitor class of chemistry including but not limited to mesotrione, sulcotrione, isoxaflutole, and pyrazolynate.
MSMA and DSMA = herbicides from the organoarsenicals chemistry family.
N/A = No suitable options available postemergence.

Example 5

Control of Volunteer Maize in a Field Planted with AAD-Maize Using Alternative Herbicides In an embodiment, volunteer transgenic maize lines (containing the Clear Field trait, Roundup Ready or other Glyphosate Tolerant Trait, Liberty Link Trait, Imidazolonine tolerant trait, or any stacked combination thereof) or volunteer conventional maize lines are controlled within a field of transgenic AAD maize (AAD-1) by the application of aryloxyphenoxypropionate herbicide (Fops) including, but not limited to; quizalofop, haloxyfop, fenoxaprop, fluazifop, et al., their stereospecific isomers or racemic mixtures, and esters, acid, or salts thereof. In addition, the Fops herbicide may be applied with another herbicide(s) to control the volunteer maize lines described above.

The specific herbicide used to control the volunteer conventional or transgenic maize line is dependent upon the type of AAD transgenic maize seed (i.e. stacked traits or alone) being planted within the field and the trait possessed by the volunteer maize line. For example an AAD-1 transgenic maize line that has been stacked with another herbicide tolerant trait such as PAT could be sprayed with a herbicide mixture containing a Fop and glufosinate, but only where the preceding volunteer plants do not contain PAT (or other glufosinate tolerant trait) and AAD-1.

The application of a given herbicide can be made before planting at pre-emergence/burndown or post-emergence after planting to control the volunteer conventional or transgenic maize lines. Table 6 lists the herbicides to be used at the different stages of planting (pre-emergence or post-emergence) to control volunteer conventional or transgenic maize. At or about a 1× Field Rate concentration of herbicide would be applied, as either a tank mix or alone, to the field for both pre-emergent and post-emergent volunteer control.

The control of conventional maize plants or transgenic maize plants containing a herbicide tolerant expression cassette within a field of AAD transgenic maize (either stacked with other herbicide tolerant traits or alone) would be applicable for the control of a herbicide tolerant transgenic monocot plant (including, but not limited too; corn, rice, sugar cane, switch grass, turf grass species, sorghum, barley, wheat, and oats, and durum) within a field being planted with an AAD monocot crop (including, but not limited too; corn, rice, sugar cane, switch grass, turf grass species, sorghum, barley, wheat, and oats, and durum). The example described above, in which volunteer transgenic herbicide tolerant maize plants are controlled in a field planted with AAD transgenic maize, is illustrative of the invention and not intended to restrict the scope of this embodiment.

TABLE 6

Control of volunteer corn (or other monocots) in AAD-1 (alone or stacked with other HT traits) corn (or other monocots)

| Previous year Corn hybrid | 2008 Corn hybrid being planted | Herbicides option - Burndown/PRE | Herbicides option - POST |
|---|---|---|---|
| | Application: alone and tank mixes | | |
| Conventional corn | AAD-1 | Glyphosate, Dims, Fops, glufosinate, paraquat | Fops |
| | AAD-1 + PAT | | Fops, glufosinate |
| | AAD-1 + GT | IMI or other ALS herbicides not recommended for corn (need to be aware of planting restrictions) | Fops, glyphosate |
| | AAD-1 + GAT + ALS | | Fops, glyphosate, ALS inhibitors not selective for in-corn application |
| | AAD-1 + AHAS | | Fops, glyphosate, IMI |
| | AAD-1 + CL | | Fops, IMI |
| | AAD-1 + PAT + GT | | Fops, glufosinate, glyphosate |
| | AAD-1 + PAT + GAT + ALS | | Fops, glufosinate, glyphosate, IMI, ALS inhibitors not selective for in-corn application |
| | AAD-1 + PAT + AHAS | | Fops, glufosinate, glyphosate, IMI |
| CL Corn | AAD-1 | Glyphosate, Dims, Fops, glufosinate, paraquat | Fops |
| | AAD-1 + PAT | | Fops, glufosinate |
| | AAD-1 + GT | other ALS herbicides not recommended for corn (need to be aware of planting restrictions) | Fops, glyphosate |
| | AAD-1 + GAT + ALS | | Fops, glyphosate, ALS inhibitors not selective for in-corn application |
| | AAD-1 + AHAS | Dims, Fops, glufosinate, paraquat | Fops, glyphosate |
| | AAD-1 + CL | | Fops |
| | AAD-1 + PAT + GT | IMI or other ALS herbicides not recommended for corn (need to be aware of planting restrictions) | Fops, glufosinate, glyphosate |
| | AAD-1 + PAT + GAT + ALS | | Fops, glufosinate, glyphosate, ALS inhibitors not selective for in-corn application |
| | AAD-1 + PAT + AHAS | | Fops, glufosinate, glyphosate |
| RR or GT Corn | AAD-1 | | Fops |
| | AAD-1 + PAT | | Fops, glufosinate |
| | AAD-1 + GT | | Fops |
| | AAD-1 + GAT + ALS | | Fops, ALS inhibitors not selective for in-corn application |
| | AAD-1 + AHAS | | Fops, IMI |
| | AAD-1 + CL | | Fops, IMI |
| | AAD-1 + PAT + GT | | Fops, glufosinate |
| | AAD-1 + PAT + GAT + ALS | | Fops, glufosinate, IMI, ALS inhibitors not selective for in-corn application |
| | AAD-1 + PAT + AHAS | | Fops, glufosinate, IMI |
| LL Corn | AAD-1 | Glyphosate, Dims, Fops, paraquat | Fops |
| | AAD-1 + PAT | | Fops |
| | AAD-1 + GT | IMI or other ALS herbicides not recommended for corn (need to be aware of planting restrictions) | Fops, glyphosate |
| | AAD-1 + GAT + ALS | | Fops, glyphosate, ALS inhibitors not selective for in-corn application |
| | AAD-1 + AHAS | | Fops, glyphosate, IMI |
| | AAD-1 + CL | | Fops, IMI |
| | AAD-1 + PAT + GT | | Fops, glyphosate |
| | AAD-1 + PAT + GAT + ALS | | Fops, glyphosate, IMI, ALS inhibitors not selective for in-corn application |
| | AAD-1 + PAT + AHAS | | Fops, glyphosate, IMI |

TABLE 6-continued

Control of volunteer corn (or other monocots) in AAD-1 (alone or stacked with other HT traits) corn (or other monocots)

| Previous year Corn hybrid | 2008 Corn hybrid being planted | Herbicides option - Burndown/PRE | Herbicides option - POST |
|---|---|---|---|
| GAT + ALS | AAD-1 | Glyphosate, Dims, Fops, glufosinate, paraquat | Fops |
| | AAD-1 + PAT | | Fops, glufosinate |
| | AAD-1 + GT | | Fops |
| | AAD-1 + GAT + ALS | | Fops, ALS inhibitors not selective for in-corn application |
| | AAD-1 + AHAS | | Fops |
| | AAD-1 + CL | | Fops |
| | AAD-1 + PAT + GT | | Fops, glufosinate |
| | AAD-1 + PAT + GAT + ALS | | Fops, glufosinate |
| | AAD-1 + PAT + AHAS | | Fops, glufosinate |
| CL (or AHAS) + PAT | AAD-1 | Glyphosate, Dims, Fops, glufosinate, paraquat other ALS herbicides not recommended for corn (need to be aware of planting restrictions) | Fops |
| | AAD-1 + PAT | | Fops |
| | AAD-1 + GT | | Fops, glyphosate |
| | AAD-1 + GAT + ALS | | Fops, glyphosate, ALS inhibitors not selective for in-corn application |
| | AAD-1 + AHAS | | Fops, glyphosate |
| | AAD-1 + CL | | Fops, IMI |
| | AAD-1 + PAT + GT | | Fops, glyphosate |
| | AAD-1 + PAT + GAT + ALS | | Fops, glyphosate, ALS inhibitors not selective for in-corn application |
| | AAD-1 + PAT + AHAS | | Fops, glyphosate |
| CL (or AHAS) + GT | AAD-1 | Dims, Fops, glufosinate, paraquat other ALS herbicides not recommended for corn (need to be aware of planting restrictions) | Fops |
| | AAD-1 + PAT | | Fops, glufosinate |
| | AAD-1 + GT | | Fops |
| | AAD-1 + GAT + ALS | | Fops, ALS inhibitors not selective for in-corn application |
| | AAD-1 + AHAS | | Fops |
| | AAD-1 + CL | | Fops |
| | AAD-1 + PAT + GT | | Fops, glufosinate |
| | AAD-1 + PAT + GAT + ALS | | Fops, glufosinate, ALS inhibitors not selective for in-corn application |
| | AAD-1 + PAT + AHAS | | Fops, glufosinate |
| GT + PAT | AAD-1 | Dims, Fops, paraquat IMI or other ALS herbicides not recommended for corn (need to be aware of planting restrictions) | Fops |
| | AAD-1 + PAT | | Fops |
| | AAD-1 + GT | | Fops |
| | AAD-1 + GAT + ALS | | Fops, ALS inhibitors not selective for in-corn application |
| | AAD-1 + AHAS | | Fops, IMI |
| | AAD-1 + CL | | Fops, IMI |
| | AAD-1 + PAT + GT | | Fops |
| | AAD-1 + PAT + GAT + ALS | | Fops, IMI, ALS inhibitors not selective for in-corn application |
| | AAD-1 + PAT + AHAS | | Fops, IMI |
| GT + CL (or AHAS) + PAT | AAD-1 | Dims, Fops, paraquat other ALS herbicides not recommended for corn (need to be aware of planting restrictions) | Fops |
| | AAD-1 + PAT | | Fops |
| | AAD-1 + GT | | Fops |
| | AAD-1 + GAT + ALS | | Fops, ALS inhibitors not selective for in-corn application |
| | AAD-1 + AHAS | | Fops |
| | AAD-1 + CL | | Fops |
| | AAD-1 + PAT + GT | | Fops |
| | AAD-1 + PAT + GAT + ALS | | Fops, ALS inhibitors not selective for in-corn application |
| | AAD-1 + PAT + AHAS | | Fops |

TABLE 6-continued

Control of volunteer corn (or other monocots) in AAD-1 (alone or stacked with other HT traits) corn (or other monocots)

| Previous year Corn hybrid | 2008 Corn hybrid being planted | Herbicides option - Burndown/PRE | Herbicides option - POST |
|---|---|---|---|
| GAT + ALS + PAT | AAD-1 | Dims, Fops, paraquat | Fops |
| | AAD-1 + PAT | | Fops |
| | AAD-1 + GT | | Fops |
| | AAD-1 + GAT + ALS | | Fops |
| | AAD-1 + AHAS | | Fops |
| | AAD-1 + CL | | Fops |
| | AAD-1 + PAT + GT | | Fops |
| | AAD-1 + PAT + GAT + ALS | | Fops |
| | AAD-1 + PAT + AHAS | | Fops |

Gene and trait footnotes:
GT = any glyphosate specific tolerance trait including Roundup Ready (CP4), TIPS EPSPS (GA21, Glytol, DMMG), Athenix's EPSPS, GAT only without ALS, GOX, glyphosate decarboxylase, etc.
ALS = double mutant ALS gene insensitive to all ALS herbicide chemistries including IMI herbicides.
AAD-1 = Aryloxyalkanoate dioxygenase gene providing tolerance to all commercial phenoxy auxin and all aryloxyphenoxypropionate (fop) herbicides.
AAD-12 = Aryloxyalkanoate dioxygenase gene providing tolerance to phenoxyacetic auxin and pyridyloxyacetic auxin herbicides.
PAT = phosphinothricin acetyltransferase gene providing tolerance to glutamine synthetase inhibitors including, but not limited to, glufosinate. Similar phenotype is provided by genes such as BAR, DSM1, DSM2, et al.
AHAS = imidazolonine specific tolerance gene associated with point mutation at S623 of ALS gene (maize sequence) or equivalent amino acid in other spp (e.g., S653 in *Arabidopsis*).
RR = Roundup Ready trait, implies utility of CP4 gene as commercially deployed either alone or in combination with other genes but imparting glyphosate only tolerance.
CL = Clearfield crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.
LL = Liberty Link trait, implies utility of either PAT or BAR gene as commercially deployed either alone or in combination with other genes but imparting only tolerance to glutamine synthetase inhibitors such as glufosinate.
STS = designates resistance to sulfonylurea herbicide chemistry with use of ALS1 gene.
Herbicide footnotes:
IMI = any imidazolonine herbicide including, but not limited to, imazapyr, imazethapyr, imazamox, imazaquin.
DIMS = cyclohexanedione class of herbicides (dims) including, but not limited to, sethoxydim, clethodim, and for the purposes of this demonstration poinoxaden.
Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.
ALS inhibitors = any ALS inhibitor to the exclusion of IMI's for the sake of this demonstration (i.e., sulfonylureas, triazolopyrimidine sulfonanalides, sulfonylaminocarbonyltriazolinone).
HPPD = p-Hydroxyphenyl pyruvate dioxygenase inhibitor class of chemistry including but not limited to mesotrione, sulcotrione, isoxaflutole, and pyrazolynate.
MSMA and DSMA = herbicides from the organoarsenicals chemistry family.
N/A = No suitable options available postemergence.

Example 5

Testing of Post-Emergent Herbicide Application on Transgenic Maize Containing AAD-1 and PAT Transgenic Hi-II maize plants containing the AAD-1 and PAT expression cassette (RB7 MAR v3::*Zea Maize* Ubiquitin Promoter v2::AAD-1 v3::*Zea Maize* Per5 3'UTR v2::Rice Actin1 Promoter v2::PAT v3::*Zea Maize* Lipase 3'UTR v1) from pDAB3404 and Hi-II non-transgenic control plants were propagated for testing. Seed were planted into Metro Mix Media (Sun Gro Horticulture Inc., Bellevue, Wash.) and subirrigated with Hoagland's solution until wet, then allowed to gravity drain. Pots were placed in a glasshouse environment set to 27° C. until the germinated plants reached the V1-V3 growth stage. At or about, the V1-V3 growth stage, the maize plants were spayed using a track sprayer and a drop down nozzle calibrated to deliver a187 L/ha solution of herbicide at the 1× Field Rate (Table 7). After treatment the plants were placed in the greenhouse and scored via visual injury assessment after 14 days. Table 7 also lists the tolerance of the plants to the applied herbicides as determined by the visual injury assessment.

TABLE 7

Graminicidal active ingredients on AAD-1 + PAT + glyphosate tol
Tolerance (−/+)

| Trt | Chemical Name | WT | 3404 | Rate (1x)/Comment |
|---|---|---|---|---|
| Select | clethodim | − | − | 26.25-52.5 g ai/ha |
| Poast | sethoxydim | − | − | 105-210 g ai/ha |
| Achieve Liquid | tralkoxydim | − | − | 100 g ai/ha |
| Pursuit | imazethapyr | −/+ | −/+ | Need higher than 70 g ai/ha rate (50% injury @ 70 g ai/ha) |
| Raptor | imazamox | − | − | 44 g ai/ha |
| Scepter | imazaquin | −/+ | −/+ | Need higher than 50 g ai/ha rate (50% injury @ 50 g ai/ha) |
| Assure II | quizalofop | − | + | 35-70 g ai/ha |
| Discover | clodinafop | − | + | 28-56 g ai/ha |
| Hoelon | diclofop-methyl | − | − | Not active on grasses |
| Fusilade DX | fluazifop-P-butyl | − | + | 105 g ai/ha |
| Gallant Super | haloxyfop-methyl R | − | + | 17.5-35 g ai/ha |

TABLE 7-continued

Graminicidal active ingredients on AAD-1 + PAT + glyphosate tol
Tolerance (−/+)

| Trt | Chemical Name | WT | 3404 | Rate (1x)/Comment |
|---|---|---|---|---|
| Puma Super | fenoxaprop-P-ethyl | − | + | 23-46 g ai/ha |
| Clincher SF | cyhalofop-butyl | − | + | 280 g ai/ha |
| Axial | pinoxaden | +/− | +/− | Not active but small amt of control on both WT and AAD-1 |
| Glyphomax XRT | glyphosate-isopropylammonium | − | + | 420-840 g ai/ha |
| Liberty | glufosinate-ammonium | − | + | 240-480 g ai/ha |
| Hoelon | diclofop-methyl | − | − | Not active on grasses |
| Fusilade DX | fluazifop-P-butyl | − | + | 105 g ai/ha |
| Gallant Super | haloxyfop-methyl R | − | + | 17.5-35 g ai/ha |
| Puma Super | fenoxaprop-P-ethyl | − | + | 23-46 g ai/ha |
| Clincher SF | cyhalofop-butyl | − | + | 280 g ai/ha |
| Axial | pinoxaden | +/− | +/− | Not active but small amt of control on both WT and AAD-1 |
| Glyphomax XRT | glyphosate-isopropylammonium | − | + | 420-840 g ai/ha |
| Liberty | glufosinate-ammonium | − | + | 240-480 g ai/ha |

Note:
3404 column contains molecular stack of AAD-1, and PAT crossed conentionally with CP4 for glyphosate tole

---

The invention claimed is:

1. A method of controlling Aryloxy Alkanoate Dioxygenase (AAD-1) volunteer corn plants, comprising Event DAS-40278-9 as available in seed deposited under ATCC deposit number PTA-10244, in a field comprising dicot plants, said volunteer corn plants comprising an AAD-1 gene, wherein said method comprises applying a herbicide to said volunteer corn plants.

2. The method of claim 1, wherein said dicot plants are selected from the group consisting of soybeans and cotton.

3. The method of claim 1, wherein said AAD-1 gene encodes a protein selected from the group consisting of SEQ ID NO:1, SEQ ID NO:2, and SEQ ID NO:3.

4. The method of claim 1, wherein said herbicide is selected from the group consisting of a cyclohexanedione and an imidazolinone.

5. The method of claim 4, wherein said herbicide is a cyclohexanedione selected from the group consisting of clethodim and sethosydim.

6. The method of claim 4, wherein said herbicide is an imidazolinone selected from the group consisting of imazethapyr, imazamox, and imazaquin.

7. The method of claim 6, wherein said dicot plants are soybeans, and said volunteer corn plants are other than imidazolinone-tolerant corn.

8. The method of claim 1, wherein said volunteer corn plants comprise a glyphosate- and/or a glufosinate-tolerance gene.

9. A method of controlling AAD-1 volunteer corn plants in a field comprising dicot plants, said volunteer corn plants comprising SEQ ID NO:4 of corn Event DAS-40278-9, wherein said method comprises applying a herbicide to said volunteer corn plants, wherein said volunteer corn plants are susceptible to said herbicide, and said dicot plants are tolerant to said herbicide.

10. The method of claim 9, wherein said herbicide is selected from the group consisting of glyphosate and glufosinate.

11. The method of claim 9, wherein said dicot plants are selected from the group consisting of soybeans and cotton.

12. The method of claim 9, wherein said herbicide is selected from the group consisting of a cyclohexanedione and an imidazolinone.

13. The method of claim 12, wherein said volunteer corn plants comprise a glyphosate- and/or a glufosinate-tolerance gene.

14. The method of claim 13, wherein said herbicide is selected from the group consisting of a cyclohexanedione and an imidazolinone.

15. The method of claim 9, wherein said herbicide is selected from the group consisting of acetolactate synthase inhibitors and acetohydroxyacid synthase inhibitors.

16. The method of claim 9, wherein said AAD-1 gene encodes a protein selected from the group consisting of SEQ ID NO:1, SEQ ID NO:2, and SEQ ID NO:3.

17. The method of claim 9, wherein said herbicide is a cyclohexanedione selected from the group consisting of clethodim and sethoxydim.

18. The method of claim 9, wherein said herbicide is an imidazolinone selected from the group consisting of imazethapyr, imazamox, and imazaquin.

19. The method of claim 18, wherein said dicot plants are soybeans, and said corn is other than imidazolinone-tolerant corn.

20. The method of claim 1, wherein said herbicide is selected from the group consisting of glyphosate and glufosinate.

21. The method of claim 1, wherein said herbicide is selected from the group consisting of acetolactate synthase inhibitors and acetohydroxyacid synthase inhibitors.

\* \* \* \* \*